US011952407B2

(12) United States Patent
Cottingham et al.

(10) Patent No.: US 11,952,407 B2
(45) Date of Patent: *Apr. 9, 2024

(54) PHARMACEUTICAL PREPARATION

(71) Applicant: Ferring International Center SA, Saint Prex (CH)

(72) Inventors: Ian Cottingham, St. Prex (CH); Daniel Plaksin, St. Prex (CH); Richard Boyd White, San Diego, CA (US)

(73) Assignee: FERRING INTERNATIONAL CENTER S.A., Saint-Prex (CH)

( * ) Notice: Subject to any disclaimer, the term of this patent is extended or adjusted under 35 U.S.C. 154(b) by 187 days.

This patent is subject to a terminal disclaimer.

(21) Appl. No.: 17/246,348

(22) Filed: Apr. 30, 2021

(65) Prior Publication Data
US 2021/0332099 A1    Oct. 28, 2021

Related U.S. Application Data

(63) Continuation of application No. 15/690,061, filed on Aug. 29, 2017, now Pat. No. 10,995,128, which is a continuation of application No. 15/238,362, filed on Aug. 16, 2016, now Pat. No. 9,771,407, which is a continuation of application No. 14/541,852, filed on Nov. 14, 2014, now Pat. No. 9,546,204, which is a continuation of application No. 12/988,218, filed as application No. PCT/GB2009/000978 on Apr. 16, 2009, now Pat. No. 8,951,967.

(60) Provisional application No. 61/045,424, filed on Apr. 16, 2008.

(30) Foreign Application Priority Data

Apr. 25, 2008 (EP) .................................. 08251528

(51) Int. Cl.
*C07K 14/59* (2006.01)
*A61K 38/00* (2006.01)

(52) U.S. Cl.
CPC .............. *C07K 14/59* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,929,028 A | 7/1999 | Skrabanja et al. |
| 5,994,128 A | 11/1999 | Fallaux et al. |
| 7,964,562 B2 | 6/2011 | Filicori |
| 7,985,732 B2 | 7/2011 | Filicori |
| 8,951,967 B2 | 2/2015 | Cottingham et al. |
| 9,546,204 B2 | 1/2017 | Cottingham et al. |
| 9,771,407 B2 | 9/2017 | Cottingham et al. |
| 10,995,128 B2 | 5/2021 | Cottingham et al. |
| 2005/0085412 A1 | 4/2005 | Loumaye et al. |
| 2008/0226681 A1 | 9/2008 | Goletz et al. |
| 2011/0105398 A1 | 5/2011 | Cottingham et al. |
| 2013/0023476 A1 | 1/2013 | Cottingham et al. |

FOREIGN PATENT DOCUMENTS

| | | |
|---|---|---|
| JP | 99/11665 | 8/2002 |
| JP | 2005-515974 | 6/2005 |
| JP | 2007/522179 | 8/2007 |
| WO | WO 1988/010270 | 12/1988 |
| WO | WO 97/00326 | 1/1997 |
| WO | WO 1998/031826 | 7/1998 |
| WO | WO 2003/035686 | 5/2003 |
| WO | WO 2003/038100 | 5/2003 |
| WO | WO 03/048348 | 6/2003 |
| WO | WO 2004/105788 | 12/2004 |
| WO | WO 2005/076013 | 8/2005 |
| WO | WO 2005/080585 | 9/2005 |
| WO | WO 2009/127826 | 10/2009 |
| WO | WO 2011/042688 | 4/2011 |
| WO | WO 2012/013742 | 2/2012 |
| WO | WO 2012/016576 | 2/2012 |
| WO | WO 2012/017058 | 2/2012 |
| WO | WO 2012/042381 | 4/2012 |
| WO | WO 2012/131306 | 10/2012 |
| WO | WO 2012/168680 | 12/2012 |
| WO | WO 2013/020996 | 2/2013 |
| WO | WO 2015/158875 | 10/2015 |

OTHER PUBLICATIONS

Bioprocess online (Per.C6 Manufacturing Platform <https://www.bioprocessonline.com/doc/perc6-manufacturing-platform-0001> (Apr. 11, 2006).
Combarnous et al., "Structure and structure-function relationships of human recombinant FSH," *Medecine sciences*, 1999, 15, 167-174 (with English summary).
De Leeuw et al., Structure-function relationship of recombinant follicle stimulating hormone (Puregon), *Molecular Human Reproduction*, 1996, 2(5), 361-369.
Jones et al., "High-Level Expression of Recombinant IgG .in the Human Cell Line PER.C6," *Biotechnol. Prog*, 2003, 19, 163-168.
Notice of Opposition in European Application No. EP16158141.8, dated Dec. 22, 2017, 5 pages.
Pau et al., "The human cell line PER.C6 provides a new manufacturing system for the production of influenza vaccines," *Vaccine*, 2001, 19, 2716-2721 (with English abstract).
Amoresano et al., "Structural characterisation of human recombinant glycohormones follitropin, lutropin and choriogonadotropin expressed in Chinese hamster ovary cells," *Eur J Biochem.*, 1996, 242:608-618.
Andersen et al., "FSH isoform composition of commercial gonadotrophin preparations: a neglected aspect?", *Reprod. Biomed. Online*, 2004, 9(2), 231-36.
Arey et al., "Induction of promiscuous G protein coupling of the follicle-stimulating hormone (FSH) receptor: a novel mechanism for transducing pleiotropic actions of FSH isoforms", *Mol. Endocrinol.*, 1997, 11(5), 517-26.

(Continued)

*Primary Examiner* — Julie Ha
*Assistant Examiner* — Tara L Martinez
(74) *Attorney, Agent, or Firm* — Foley & Lardner LLP

(57) ABSTRACT

Preparations including recombinant FSH (rFSH).

5 Claims, 9 Drawing Sheets

Specification includes a Sequence Listing.

(56) References Cited

OTHER PUBLICATIONS

Avis, K. E., "Parenteral Preparations—History, Administration, Components, Production, Quality Control, Packaging, Labeling", *Remington's Pharmaceutical Sciences*, fifteenth edition, 1975, 1461-1487.

Baenziger, et al., "Pituitary glycoprotein hormone oligosaccharides: structure, synthesis and function of the asparagine-linked oligosaccharides on lutropin, follitropin and thyrotropin", *Biochim. Biophys. Acta.*, 1988, 947(2), 287-306.

Bassett et al., "Continued improvements in the quality and consistency of follitropin alfa, recombinant human FSH", *Reprod. Biomed. Online*, 2005, 10(2), 169-77.

Bragonzi et al., "A new Chinese hamster ovary cell line expressing α2,6-sialyltransferase used as universal host for the production of human-like sialylated recombinant glycoproteins," Biochimica et Biophysica Acta, 2000, 1474: 273-282.

Chin et al., "Biological activity and metabolic clearance of recombinant human follicle stimulating hormone produced in Sp2/0 myeloma cells," Cytotechnology, 1996, 21(2): 171-182.

Chitlaru et al., "Overloading and removal of N-glycosylation targets on human acetylcholinesterase : effects on glycan composition and circulatory residence time," Biochem J., 2002, 363:619-631.

Combarnous, Y., "Structure et relations structure-activité des hormones folliculo-stimulantes recombinantes humaines", *Médecine/Sciences*, 1999, 15, 167-74 (with English translation).

D'Antonio et al., "Biological characterization of recombinant human follicle stimulating hormone isoforms", *Hum. Reprod.*, 1999, 14, 1160-67.

Dalpathado et al., "Comparative glycomics of the glycoprotein follicle stimulating hormone: glycopeptide analysis of isolates from two mammalian species", *Biochem.*, 2006, 45(28), 8665-73.

Damián-Matsumura et al., "Oestrogens regulate pituitary alpha2,3-sialyltransferase messenger ribonucleic acid levels in the female rat", *J. Mol. Endocrinol.*, 1999, 23(2), 153-65.

D'Antonio et al., "Biological Characterization of Recombinant Human Follicle Stimulating Hormone Isoforms", *Human Reproduction*, 1999, 14, 1160-1167.

De Leeuw et al., "Structure-function relationship of recombinant follicle stimulating hormone (Puregon®)", *Mol. Hum. Reprod.*, 1996, 2, 361-69.

Deardoff, D. L., "Isotonic Solutions—Freezing Point, Calculations, Tonicity Testing, Methods", *Remington's Pharmaceutical Sciences*, fifteenth edition, 1975, 1405-1412.

Dias, J. A. and Van Roey, P., "Structural biology of human follitropin and its receptor", *Arch. Med. Res.*, 2001, 32(6), 510-19.

Dickey et al., "Highly purified human-derived follicle-stimulating hormone (Bravelle®) has equivalent efficacy to follitropin-beta (Follistim®) in infertile women undergoing in vitro fertilization," Reproductive Biol Endocrinol., 2003, 1:63, 8 pages.

EMD Serono Canada, Inc., "Product Monograph: PrGonal-f® Pen," Submission Control No. 114679, dated Jun. 29, 2007, 37 pp.

EMEA, "Scientific Discussion," EMEA Review of PUREGON® (available online at http://www.ema.europa.eu/docs/en_GB/document_library/EPAR_-_Scientific_Discussion/human/000086/WC500045613.pdf), 2005, 16 pp.

European File History for Application No. 09733497.3, retreived on Jul. 30, 2014, 512 pp.

European File History for Application No. 13193214.7, retreived on Jul. 30, 2014, 237 pp.

Expert Declaration (Exhibit No. 52) and Curriculum Vitae (Exhibit No. 52a) of Yves Combarnous dated Aug. 28, 2009 (27 pgs.).

Extended European Search Report in Application No. 14178729.1, dated Nov. 4, 2014, 9 pages.

Ferring Pharmaceuticals Inc., Product Information Bravelle® (urofollitropin for injection, purified) For Subcutaneous or Intramuscular Injection, Jun. 2012, 2 pp.

Fiddes and Goodman, "The cDNA for the Beta-Subunit of Human Chorionic Gonadotropin Suggests Evolution of a Gene by Readthrough into the 3'-Untranslated Region", Nature, 1980, 286, 684-387.

Fiddes et al., "Isolation, cloning and sequence analysis of the cDNA for the alpha-subunit of human chorionic gonadotropin", *Nature*, 1979, 281, 351-56.

Flack et al., "Increased biological activity due to basic isoforms in recombinant human follicle-stimulating hormone produced in a human cell line", *J. Clin. Endocrinol. Metab.*, 1994, 3(79), 756-60.

Fox et al., "Three-dimensional structure of human follicle-stimulating hormone", *Mol. Endocrinol.* 2001, 15(3), 378-89.

Fukuta et al., "Genetic engineering of CHO cells producing human interferon-y by transfection of sialyltransferases," Glycoconjugate Journal, 2000, 17: 895-904.

Grabenhorst et al., "Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal(beta 1-4)GlcNAc(beta 1-2)Man(alpha 1-3)-branch of diantennary oligosaccharides from secreted recombinant beta-trace protein", *Eur. J. Biochem.*, 1995, 232(3), 718-25.

Green, E. D et al., "Asparagine-linked oligosaccharides on lutropin, follitropin, and thyrotropin. II. Distributions of sulfated and sialylated oligosaccharides on bovine, ovine, and human pituitary glycoprotein hormones", *J. Biol. Chem.*, 1988, 263(1), 36-44.

Grundmann et al., "Complete cDNA sequence encoding human beta-galactoside alpha-2,6-sialyltransferase", *G Nucleic Acids Res.*, 1990, 18(3), 667.

Haber, FDA Division of Metabolic and Endocrine Drugs; Chemistry Review for NDA 21-289 Bravelle (urofollitropin for injection, purified), Ferring Pharmaceuticals, Inc, dated Apr. 25, 2002, 31 pp.

Hard et al., "Isolation and structure determination of the intact sialylated N-linked carbohydrate chains of recombinant human follitropin expressed in Chinese hamster ovary cells," Eur. J. Biochem., 1990, 193: 263-271.

Hard et al., "The Carbohydrate Chains of the [beta] Subunit of Human Chorionic Gonadotropin Produced by the Choriocarcinoma Cell Line BeWo. Novel O-linked and Novel Bisecting-GlcNAc-Containing N-linked Carbohydrates", *European Journal of Biochemistry* DE, 1992, 205(2), 1992, 785-798.

Harvey, S. C., "Cardiovascular Drugs—Antihypertensive and Hypotensive Drugs, Peripheral Vasodilators, Coronary Drugs, Cardiac Glycosides, Antiarrhythmic Drugs, Drugs Affecting Blood Lipids, Miscellaneous Drugs", *Remington's Pharmaceutical Sciences*, fifteenth edition, 1975, 807-820.

Harvey, S. C., "Sympathomimetic Drugs", *Remington's Pharmaceutical Sciences*, fifteenth edition, 1975, 780-797.

Horseman et al., "A biological, immunological and physic-chemical comparison of the current clinical batches of the recombinant FSH preparations Gonal-F and Puregon", *Hum. Reprod.*, 2000, 15(9), 1898-1902.

Howles, C. M., "Genetic engineering of human FSH (Gonal-F®)", *Hum. Reprod. Update*, 1996, 2(2), 172-91.

International Search Report dated Jan. 31, 2011 for International Appln. No. PCT/GB2010/001854 (4 pgs.).

International Search Report dated Jun. 30, 2009 for International Appl. No. PCT/GB2009/000978 (8 pgs.).

Japanese Office Action in Japanese Application No. 2011-504527, dated Aug. 2, 2016, 26 pages (English Translation).

Jones et al., "High level expression of recombinant IgG in the human cell line Per.C6", *Biotechnol. Progress*, 2003, 19, 163-68.

Kagawa et al., "Comparative study of the asparagine-linked sugar chains of natural human interferon-beta 1 and recombinant human interferon-beta 1 produced by three different mammalian cells", *J. Biol. Chem.*, 1988, 263(33), 17508-15.

Keene et al., "Expression of Biologically active Human Follitropin in Chinese Hamster Ovary Cells", *J. Biol. Chem.*, 1989, 264(9), 4769-75.

Kessler et al., "Structure and location of the O-glycosidic carbohydrate units of human chorionic gonadotropin," *J Biol. Chem.*, Aug. 1979, 254(15):7909-7914.

Kitagawa et al., "Cloning of a novel alpha 2,3-sialyltransferase that sialylates glycoprotein and glycolipid carbohydrate groups", *J. Biol. Chem.*, 1994, 269(2), 1394-1401.

(56) References Cited

OTHER PUBLICATIONS

Lee et al., "Alteration of terminal glycosylation sequences on N-linked oligosaccharides of Chinese hamster ovary cells by expression of beta-galactoside alpha 2,6-sialyltransferase", *J. Biol. Chem.*, 1989, 264(23), 13848-55.

Lowry et al., "Protein measurement with the Folin phenol reagent", *J. Biol. Chem.*, 1951, 193(1), 265-75.

Lowry et al., "Purification of anterior pituitary and hypothalamic hormones", *J. Clin. Pathol., Suppl. (Assoc. Clin. Pathol.)*, 1976, 30(7), 16-21.

Olijve et al., "Molecular biology and biochemistry of human recombinant follicle stimulating hormone (Puregon®)", *Mol. Hum. Reprod.*, 1996, 2(5), 371-82.

Opposition filed on behalf of Merck Serono SA, against EP Patent 2 268 666, dated Dec. 8, 2014, 20 pages.

Otto et al., "Sialylated complex-type N-Glycans enhance the signalling activity of soluble intercellular adhesion molecule-1 in mouse astrocytes," *J Biol. Chem.*, 2004, 270(34):35201-35209.

Pierce et al., "Glycoprotein hormones: structure and function", *Ann. Rev. Biochem.*, 1981, 50, 465-95.

Pricer et al., "The binding of desialylated glycoproteins by plasma membranes of rat liver", *J. Biol. Chem.*, 1971, 246(15), 4825-33.

Rathnam et al., "Primary amino acid sequence of follicle-stimulating hormone from human pituitary glands. I. alpha subunit", *J. Biol. Chem.*, 1975, 250(17), 6735-46.

Raymond et al., "Production of Highly Sialylated Monoclonal Antibodies," InTech, 2012, Chpt. 17, pp. 397-418.

Regoeczi et al., "Elimination of asialofetuin and asialoorosomucoid by the intact rat. Quantitative aspects of the hepatic clearance mechanism", *Biochim. Biophys. Acta.*, 1978, 541(3), 372-84.

Reinke et al., "Analysis of Cell Surface N-glycosylation of the Human Embryonic Kidney 293T Cell Line," *J Carbohydrate Chem.*, 2011, 30:218-232.

Royle et al., "Detailed Structural Analysis of N-Glycans Released From Glycoproteins in SDS-Page Gel Bands Using HPLC Combined With Exoglycosidase Array Digestions", *Methods Mol. Biol.: Glycobiol. Protocols*, 2006, 347, 125-44.

Ryan et al., "Structure-function relationships of gonadotropins", *Recent Prog Horm Res.*, 1987, 43, 383-429.

Saxena et al., "Amino acid sequence of the beta subunit of follicle-stimulating hormone from human pituitary glands", *J. Biol. Chem.*, 1976, 251(4), 993-1005.

Stanton et al., "Application of a sensitive HPLC-based fluorometric assay to determine the sialic acid content of human gonadotropin isoforms," *J. Biochem. Biophys. Methods*, 1995, 30:37-48.

Steelman et al., "Assay of the follicle stimulating hormone based on the augmentation with human chorionic gonadotropin", *Endocrinol.*, 1953, 53(6), 604-616.

Steer et al., "Studies on a mammalian hepatic binding protein specific for asialoglycoproteins. Evidence for receptor recycling in isolated rat hepatocytes", *J. Biol. Chem.*, 1980, 255(7), 3008-13.

Svensson et al., "Organization of the beta-galactoside alpha 2,6-sialyltransferase gene. Evidence for the transcriptional regulation of terminal glycosylation", *J. Biol. Chem.*, 1990, 265(34), 20863-68.

Swiech et al., "Human cells: New platform for recombinant therapeutic protein production," *Protein Expression Purification*, 2012, 84:147-153.

Swinyard, "Respiratory Drugs—Stimulants, Expectorants, Antitussives, Gases", *Remington's Pharmaceutical Sciences*, fifteenth edition, 1975, 798-806.

Takeuchi et al., "Comparative study of the asparagine-linked sugar chains of human erythropoietins purified from urine and the culture medium of recombinant Chinese hamster ovary cells", *J. Biol. Chem.* 1988, 263(8), 3657-63.

Thomas and Smart, "Appraisal of state-of-the-art: HEK293 cell line: A vehicle for the expression of recombinant proteins," *J. Pharmacol. Toxicol. Methods*, 2005, 51, 187-200.

Timossi et al., "A naturally occurring basically charged human follicle-stimulating hormone (FSH) variant inhibits FSH-induced androgen aromatization and tissue-type plasminogen activator enzyme activity in vitro", *Neuroendocrinol.*, 1998, 67(3), 153-63.

Timossi et al., "Differential effects of the charge variants of human follicle-stimulating hormone", *J. Endocrinol.*, 2000, 165(2), 193-205.

Ulloa-Aguirre et al., "Biological characterization of the naturally occurring analogues of intrapituitary human follicle stimulating hormone", *Hum. Reprod.*, 1992, 7(1), 23-30.

Ulloa-Aguirre et al., "Endocrine regulation of gonadotropin glycosylation", *Arch. Med. Res.*, 2001, 32(6), 520-32.

Ulloa-Aguirre et al., "Follicle-stimulating isohormones: characterization and physiological relevance", *Endocr Rev.*, 1995, 16(6), 765-87.

Ulloa-Aguirre et al., "Immunological and biological potencies of the different molecular species of gonadotrophins", *Hum. Reprod.*, 1988, 3, 491-501.

Ulloa-Aguirre et al., "Impact of carbohydrate heterogeneity in function of follicle-stimulating hormone: studies derived from in vitro and in vivo models", *Biol Reprod.*, 2003, 69(2), 379-89.

Van Lenten et al., "The binding of desialylated glycoproteins by plasma membranes of rat liver. Development of a quantitative inhibition assay", *J. Biol. Chem.*, 1972, 247(14), 4633-40.

Varki, "Mini Review: Diversity in the sialic acids," *Glycobiol.*, 1992, 2(1):25-40.

Wide et al., "Change in electrophoretic mobility of human follicle-stimulating hormone in serum after administration of gonadotropin-releasing hormone", *J. Clin. Endocrinol. Metab.*, 1990, 70, 271-76.

Wide et al., "More basic forms of both human follicle-stimulating hormone and luteinizing hormone in serum at midcycle compared with the follicular or luteal phase", *J. Clin. Endocrinol. Metab.*, 1993, 76, 885-89.

Wide et al., "Sulfonation and sialylation of gonadotropins in women during the menstrual cycle, after menopause, and with polycystic ovarian syndrome and in men", *J. Clin. Endocrinol. Metab.*, 2007, 92(11), 4410-17.

Zambrano et al., "Receptor binding activity and in vitro biological activity of the human FSH charge isoforms as disclosed by heterologous and homologous assay systems: Implications for the structure-function relationship of the FSH variants", *Endocrine*, 1999, 10(2), 113-21.

Zhang et al., "Stable expression of human alpha-2,6-sialyltransferase in Chinese hamster ovary cells: functional consequences for human erythropoietin expression and bioactivity", *Biochim. Biophys. Acta.*, 1998, 1425(3), 441-52.

FSH expression vector

α2,3-sialyltransferase (ST3GAL4) expression vector

α2,6-sialyltransferase (ST6GAL1) expression vector

PHARMACEUTICAL PREPARATION

CROSS-REFERENCE TO RELATED APPLICATIONS

This application is a continuation of U.S. patent application Ser. No. 15/690,061, filed on Aug. 29, 2017 (now U.S. Pat. No. 10,995,128), which is a continuation of U.S. patent application Ser. No. 15/238,362, filed on Aug. 16, 2016 (now U.S. Pat. No. 9,771,407), which is a continuation of U.S. patent application Ser. No. 14/541,852, filed on Nov. 14, 2014 (now U.S. Pat. No. 9,546,204), which is a continuation of U.S. patent application Ser. No. 12/988,218, filed on Jan. 7, 2011 (now U.S. Pat. No. 8,951,967) which is the National Phase under 35 U.S.C. § 371 of PCT International Patent Application Number PCT/GB2009/000978, filed internationally on Apr. 16, 2009, and claims benefit of U.S. Provisional Application Ser. No. 61/045,424, filed on Apr. 16, 2008, and European Application No. 08251528.9, filed on Apr. 25, 2008. Each of the prior applications is hereby incorporated by reference in its entirety.

TECHNICAL FIELD

The present invention relates to gonadotrophins for use in the treatment of infertility. In particular it relates to follicle stimulating hormone (FSH).

BACKGROUND

The gonadotrophins are a group of heterodimeric glycoprotein hormones which regulate gonadal function in the male and female. They include follicle stimulating hormone (FSH), luteinising hormone (LH) and chorionic gonadotrophin (CG).

FSH is naturally secreted by the anterior pituitary gland and functions to support follicular development and ovulation. FSH comprises a 92 amino acid alpha sub-unit, also common to the other glycoprotein hormones LH and CG, and a 111 amino acid beta sub-unit unique to FSH that confers the biological specificity of the hormone (Pierce and Parsons, 1981). Each sub-unit is post translationally modified by the addition of complex carbohydrate residues. Both subunits carry 2 sites for N-linked glycan attachment, the alpha sub-unit at amino acids 52 and 78 and the beta sub-unit at amino acid residues 7 and 24 (Rathnam and Saxena, 1975, Saxena and Rathnam, 1976). FSH is thus glycosylated to about 30% by mass (Dias and Van Roey. 2001. Fox et al. 2001).

FSH purified from post-menopausal human urine has been used for many years in infertility treatment; both to promote ovulation in natural reproduction and to provide oocytes for assisted reproduction technologies. Two recombinant versions of FSH, GONAL-F® (Serono) and PUREGON™ (Organon) became available in the mid-1990's. These are both expressed in Chinese hamster ovary (CHO) cells (Howles, 1996).

There is considerable heterogeneity associated with FSH preparations which relates to differences in the amounts of various isoforms present. Individual FSH isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

Glycosylation of natural FSH is highly complex. The glycans in naturally derived pituitary FSH can contain a wide range of structures that can include combinations of bi-, tri- and tetra-antennary glycans (Pierce and Parsons, 1981. Ryan et al., 1987. Baenziger and Green, 1988). The glycans can carry further modifications: core fucosylation, bisecting glucosamine, chains extended with acetyl lactosamine, partial or complete sialylation, sialylation with α2,3 and α2,6 linkages, and sulphated galactosamine substituted for galactose (Dalpathado et al., 2006). Furthermore, there are differences between the distributions of glycan structures at the individual glycosylation sites. A comparable level of glycan complexity has been found in FSH derived from the serum of individuals and from the urine of post-menopausal women (Wide et al., 2007).

The glycosylation of recombinant FSH products reflects the range of glycosyl-transferases present in the host cell line. Existing rFSH products are derived from engineered Chinese hamster ovary cells (CHO cells). The range of glycan modifications in CHO derived rFSH are more limited than those found on the natural products, derived either from pituitary extracts or urine. Examples of the reduced glycan heterogeneity found in CHO derived rFSH include a lack of bisecting glucosamine and a reduced content of core fucosylation and acetyl lactosamine extensions (Hard et al., 1990). In addition, CHO cells are only able to add sialic acid using the α2,3 linkage (Kagawa et al, 1988, Takeuchi et al, 1988, Svensson et al., 1990). This is different from naturally produced FSH which contains glycans with a mixture of α2,3 and α2,6-linked sialic acid.

It has been demonstrated that a recombinant FSH preparation (Organon) differs in the amounts of FSH with an isoelectric point (pi) of below 4 (considered the acidic isoforms) when compared to pituitary, serum or post-menopausal urine FSH (Ulloa-Aguirre et al. 1995). The amount of acidic isoforms in the urinary preparations was much higher as compared to the recombinant products, GONAL-F® (Serono) and PUREGON™ (Organon) (Andersen et al. 2004). This must reflect a lower molar content of sialic acid in the rFSH since the content of negatively-charged glycan modified with sulphate is low in FSH. The lower sialic acid content, compared to natural FSH, is a feature of both commercially available FSH products and therefore must reflect a limitation in the manufacturing process (Bassett and Driebergen, 2005).

There is a large body of scientific work which analyses and tries to explain the variations in FSH glycosylation between individuals and changes over the course of an ovulation cycle. One of the major discussions relates to the observation that FSH concentration and sialic acid content both decrease during the pre-ovulatory phase of the cycle. The decreased sialic acid content results in a more basic FSH which is both cleared more rapidly and, in vitro at least, is more potent at the target receptor (Zambrano et al. 1996). The question as to the biological relevance of these changes and how they may be involved in selecting the dominant follicle remains unresolved (reviewed by Ulloa-Aguirre, 2003).

The circulatory life-time of FSH has been documented for materials from a variety of sources. Some of these materials have been fractionated on the basis of overall molecular charge, as characterised by their pI, in which more acid equates to a higher negative charge. As previously stated the major contributor to overall molecular charge is the total sialic content of each FSH molecule. For instance, rFSH (Organon) has a sialic acid content of around 8 mol/mol, whereas urine-derived FSH has a higher sialic acid content (de Leeuw et al. 1996). The corresponding plasma clearance rates in the rat are 0.34 and 0.14 ml/min (Ulloa-Aguirre et al. 2003). In another example where a sample of recombinant FSH was split into high and low pI fractions, the in vivo potency of the high pI (lower sialic acid content) fraction was decreased and it had a shorter plasma half-life (D'Antonio et al. 1999). It has also been reported that the more basic FSH circulating during the later stages of the ovulation cycle is due to the down-regulation of α2,3 sialyl-transferase in the anterior pituitary which is caused by increasing levels of estradiol (Damian-Matsumara et al. 1999. Ulloa-Aguirre et al. 2001). Results for the α2,6 sialyl-transferase have not been reported.

The total sialic acid content of FSH and rFSH is not directly comparable since sialic acids are commonly linked in two ways. Pituitary/serum/urinary FSH contain both α2,3 and α2,6-linked sialic acid, with a predominance of the former. However, CHO cell derived recombinants only contain α2,3 (Kagawa et al, 1988, Takeuchi et al, 1988, Svensson et al., 1990). This is another difference between natural and current recombinant products in addition to the lower overall sialic acid content of the latter.

CHO cells are commonly used for the production of pharmaceutical human recombinant proteins. Structural analysis has identified that sialic acid is exclusively attached by a α2,3-linkage. (Kagawa et al, 1988, Takeuchi et al, 1988, Svensson et al., 1990). Many human glycoproteins contain a mixture of both α2,3- and α2,6-linkages. Therefore recombinant proteins expressed using the CHO system will differ from their natural counterparts in their type of terminal sialic acid linkages. This is an important consideration in the production of biologicals for pharmaceutical use since the carbohydrate moieties may contribute to the pharmacological attributes of the molecule.

SUMMARY

The present disclosure provides recombinant FSH (rFSH) including α2,3- and α2,6-sialylation and preparations that include recombinant FSH (rFSH) including α2,3- and α2,6-sialylation. The present disclosure further provides pharmaceutical compositions that include recombinant FSH (rFSH) including α2,3- and α2,6-sialylation. The present disclosure also provides methods of treatment of infertility that include administering to a subject a composition including the recombinant FSH disclosed herein. In addition, the present application provides a method of producing recombinant FSH as disclosed herein which includes the step of producing or expressing the rFSH in a human cell line.

DETAILED DESCRIPTION

It is desirable to have a rFSH product that more closely replicates or mimics the physiochemical and pharmacokinetic profile of the product produced from human urine. It is desirable to have a rFSH product that has improved pharmacokinetic property or properties compared to the known recombinant product.

According to the present invention there is provided recombinant FSH ("rFSH" or "recFSH") including α2,3 sialylation and α2,6 sialylation and, optionally, α2,8 sialylation. The rFSH (or rFSH preparation) according to the invention may have 10% or more of the total sialylation being α2,3-sialylation, for example 65-85% of the total sialylation may be α2,3-sialylation. The rFSH (or rFSH preparation) of the invention may have 50% or less of the total sialylation being α2,6-sialylation, for example 15-35% of the total sialylation may be α2,6-sialylation. The rFSH (or rFSH preparation) of the invention may have 5% or less of the total sialylation being α2,8-sialylation, for example 0.1-4% of the total sialylation may be α2,8-sialylation. The rFSH (or rFSH preparation) according to the invention may have a sialic acid content [expressed in terms of a ratio of moles of sialic acid to moles of protein] of 6 mol/mol or greater, for example of between 6 mol/mol and 15 mol/mol.

Figure 4:
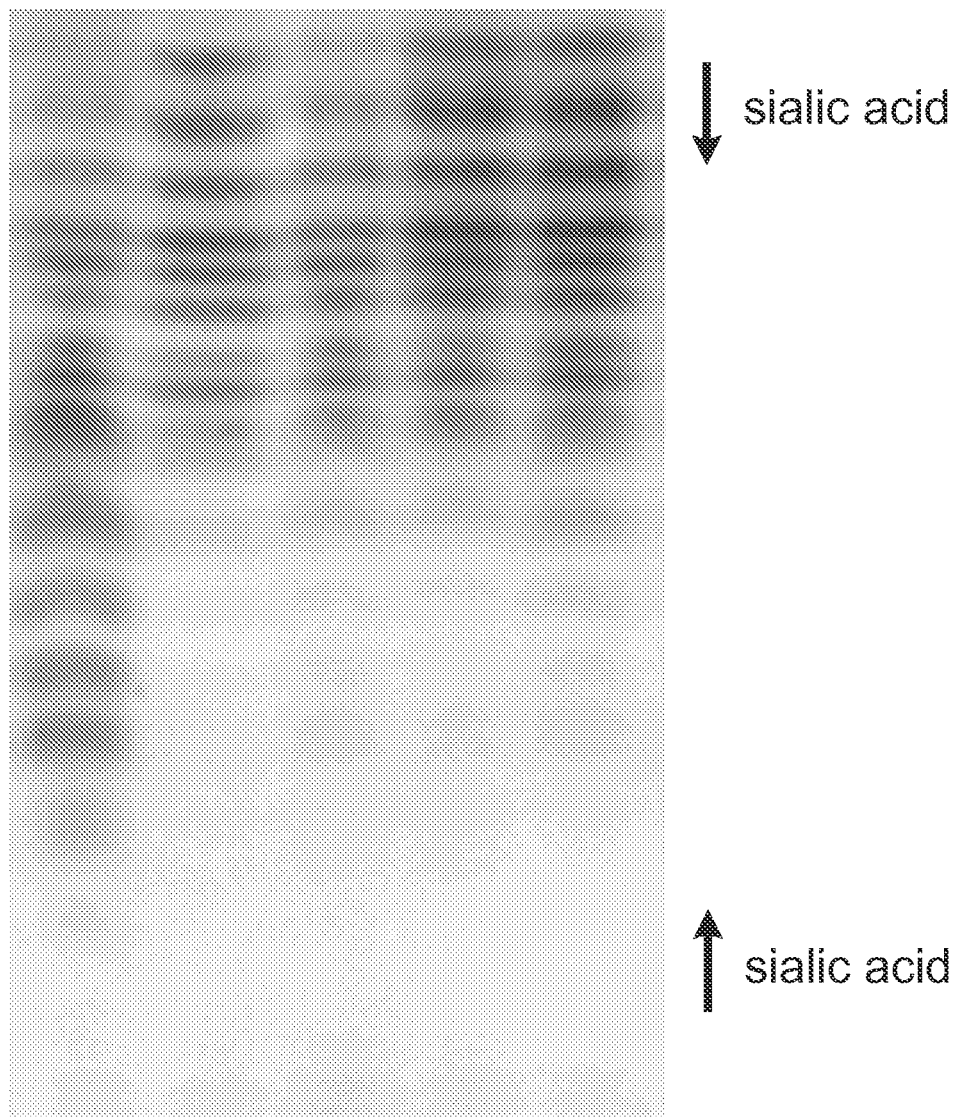
FIG. 4 is a representation of an isoelectric focusing gel showing the results of recombinant FSH produced by PER.C6® cells stably expressing FSH.
Figure 5:
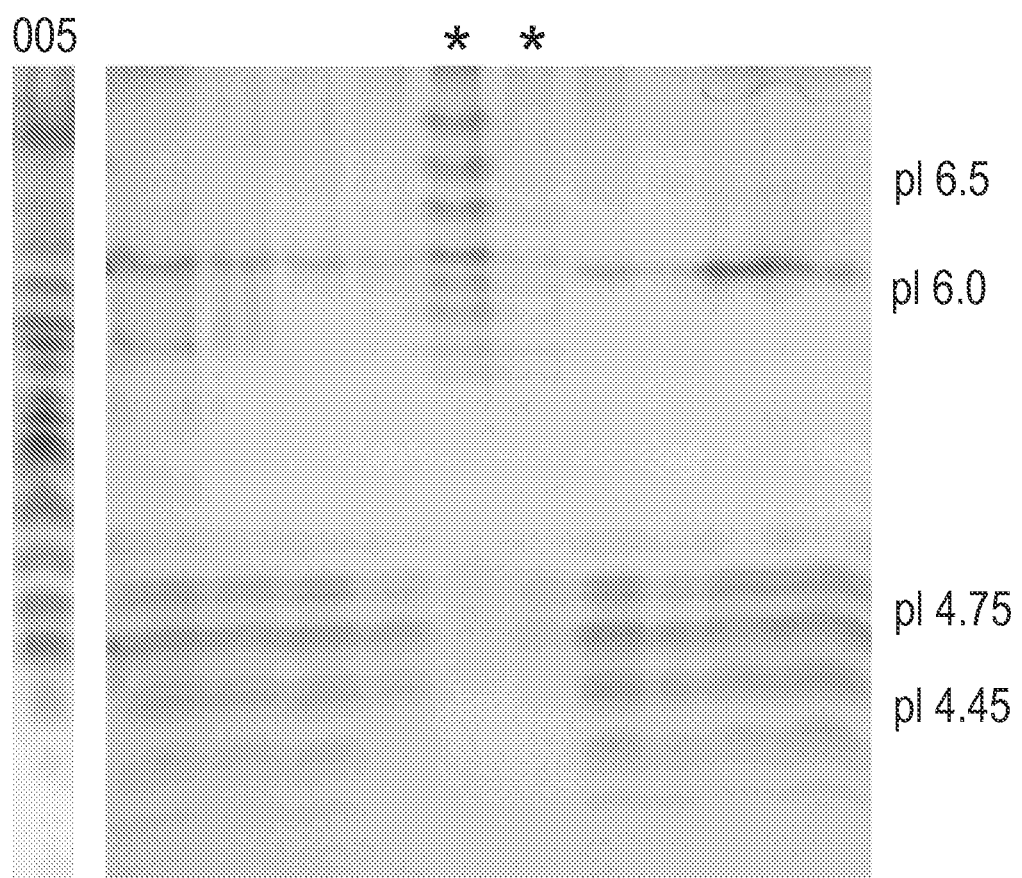
FIG. 5 is a representation of an isoelectric focusing gel that shows clones analyzed by isoelectric focusing of recombinant FSH produced by PER.C6® cells stably expressing FSH after engineering with α2,3- or α2,6-sialyltransferase.
Figure 7:
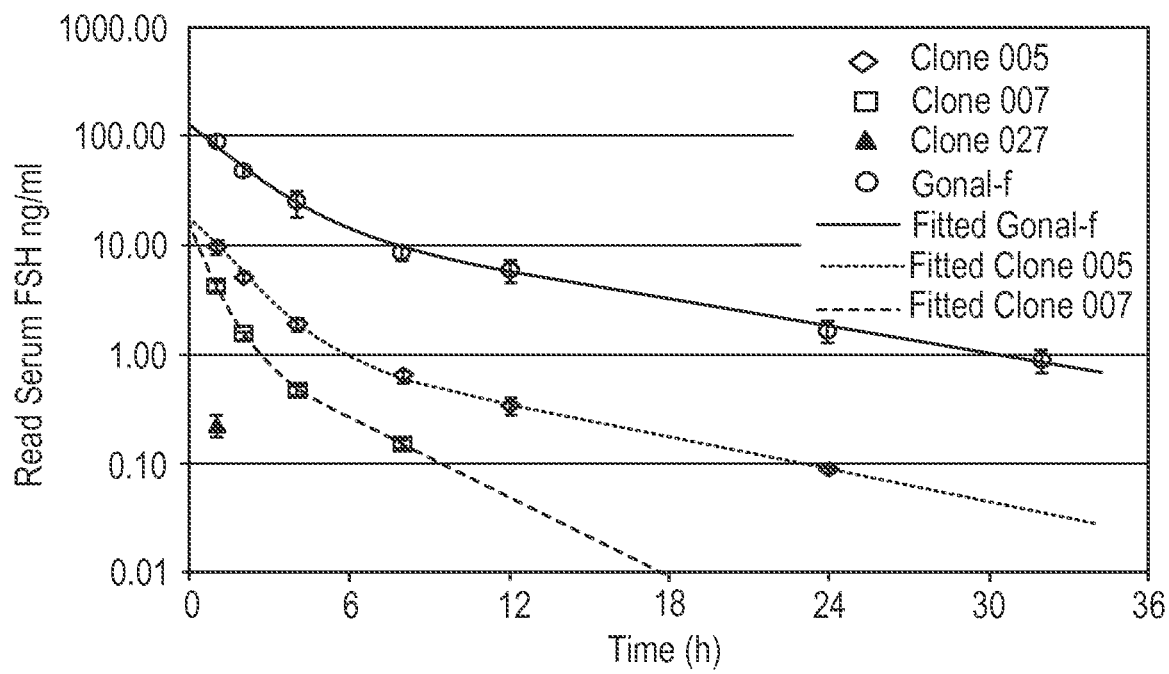
FIG. 7 is a graph that shows metabolic clearance rates (MCRs) of PER.C6® FSH samples.
Figure 8:
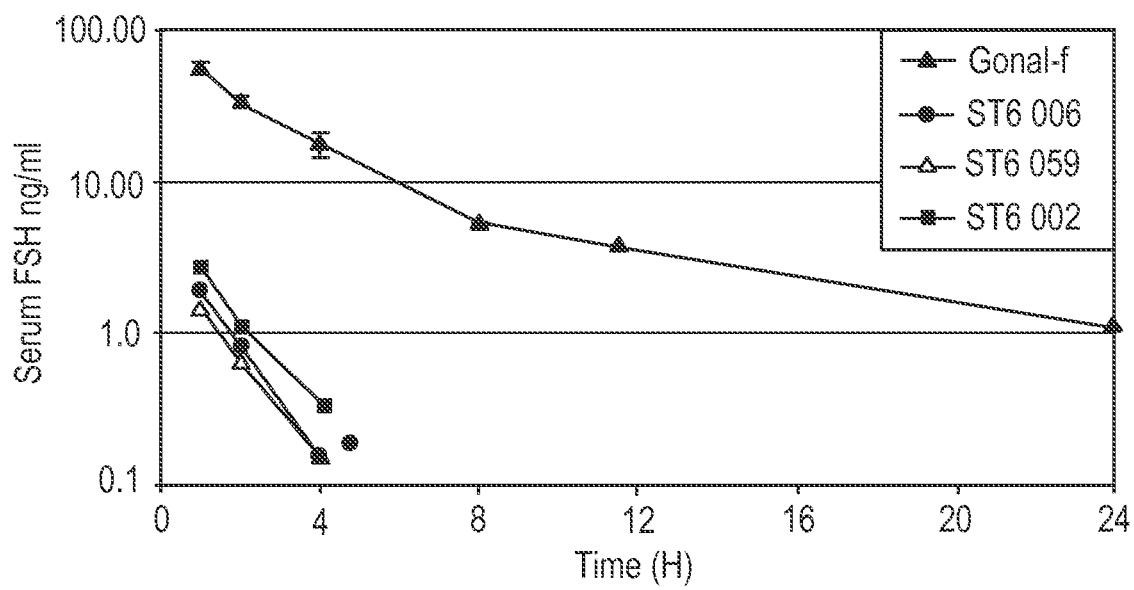
FIG. 8 is a graph that shows MCRs of α2,6-sialytransferase engineered PER.C6® FSH samples.
Figure 9:
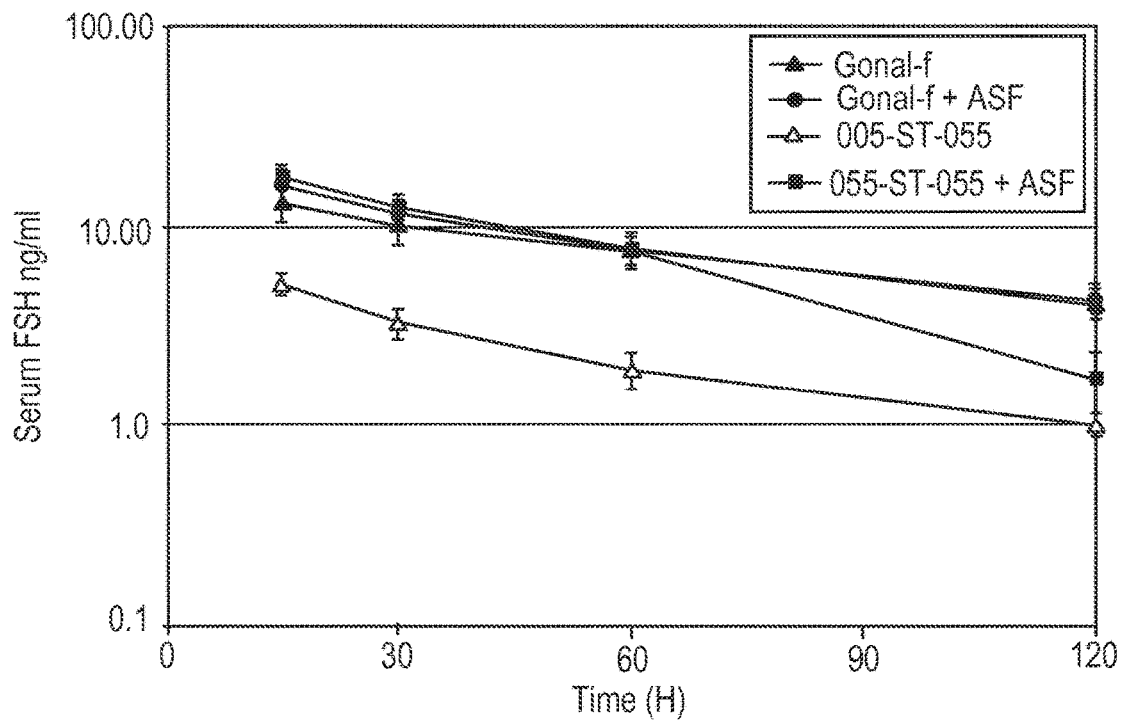
FIG. 9 is a graph that shows MCRs of α2,6-sialytransferase engineered PER.C6® FSH samples.

The applicants have found that the type of sialic acid linkage, α2,3- or α2,6-, can have a dramatic influence on biological clearance of FSH. Human cell lines, as opposed to CHO cell lines, can express recombinant FSH with sialic acids attached by both α2,3 and α2,6 linkages. In Example 4 a recombinant FSH cell line was made which expressed FSH containing glycans with low levels of both α2,3- and α2,6-linked sialic acid (FIG. 6). This basic material, with limited sialic acid content (FIG. 4) was cleared very quickly from the circulation in rat as would be predicted (FIG. 7). The cell line was then subjected to a second engineering step with the addition of the gene encoding for the α2,6-sialyltransferase (Example 5). The resulting rFSH was highly sialylated showing sialic acid content and pI distribution comparable with urinary FSH (FIG. 5). However, the material was cleared very rapidly from circulation of rats at a rate comparable to the original material which had low sialic acid content (FIG. 8). This was an unexpected observation since it is known that a proportion of sialic acid on natural and biologically active FSH is α2,6-linked. The clearance of the α2,6-sialylated rFSH was found to be mediated by the asialoglycoprotein (ASGP) receptor found in the liver (Example 9). This was demonstrated by transient blockade of the ASGP receptors using an excess of another substrate for the receptor. With the receptor blocked by asialofetuin, the expected clearance for the highly-sialylated material was restored (FIG. 9). This was maintained for several hours until the blockade was overcome and the α2,6 linked highly sialylated rFSH resumed its rapid clearance.

Recombinant FSH with a mixture of both α2,3 and α2,6-linked sialic acid was made by engineering a human cell line to express both rFSH and α2,3 sialyltransferase (Example 4 and 5). The expressed product is highly acidic and carries a mix of both α2,3- and α2,6-linked sialic acids; the latter provided by the endogenous sialyl transferase activity (FIG. 6). This has two advantages over rFSH expressed in conventional CHO cells: first the material is more highly sialylated due to the combined activities of the two sialyltransferases; and secondly the material more closely resembles the natural FSH. This is likely to be more biologically appropriate compared to CHO cell derived recombinant products that have produce only α2,3 linked sialic acid (Kagawa et al, 1988, Takeuchi et al, 1988, Svensson et al., 1990) and have decreased sialic acid content (Ulloa-Aguirre et al. 1995, Andersen et al. 2004).

The applicants have surprisingly found that rFSH of the invention may more closely replicate or mimic the physiochemical and pharmacokinetic profile of the natural human urinary product than other recombinant products. In other words, rFSH of the invention may be closer to the "natural" FSH. This may have significant advantages regarding dosing etc. Further, a more "natural" or more "human" product may be more desirable to the patient, who may desire therapy, although in a sense artificial, to be as "natural" as possible. There may be other advantages (e.g. pharmacokinetic advantages) in a recombinant product having carbohydrate (e.g. glycan) structure which is closer to natural (e.g. human urinary) FSH than other recombinant products.

The invention is thus a recombinant version of FSH which carries a mix of α2,3 and α2,6 sialic acid and therefore more closely resembles natural FSH. It is expected that the use of this compound for controlled ovarian stimulation, in IVF techniques, and ovulation induction will result in a more natural stimulation of the ovary compared to existing recombinant products.

According to the present invention there is provided recombinant FSH ("rFSH" or "recFSH") (and/or a recombinant FSH preparation) including α2,3 sialylation and α2,6 sialylation. The rFSH or rFSH preparation may optionally further include α2,8 sialylation.

Herein the term "recombinant FSH preparation" includes a preparation for e.g. pharmaceutical use which includes recombinant FSH. In embodiments of the invention, the rFSH may be present as a single isoform or as a mixture of isoforms.

The rFSH (or rFSH preparation) according to the invention may have a sialic acid content [expressed in terms of a ratio of moles of sialic acid to moles of protein] of 6 mol/mol or greater (Example 8), for example between 6 mol/mol and 15 mol/mol, e.g. between 8 mol/mol and 14 mol/mol, for example between 10 mol/mol and 14 mol/mol, e.g. between 11 mol/mol and 14 mol/mol, e.g. between 12 mol/mol and 14 mol/mol, e.g. between 12 mol/mol and 13 mol/mol. The rFSH of the invention may be produced or expressed in a human cell line.

The rFSH (or rFSH preparation) according to the invention may have 10% or more of the total sialylation being α2,3-sialylation. For example, 20, 30, 40, 50, 60, 70, 80 or 90% or more of the total sialylation may be α2,3-sialylation. The rFSH (or rFSH preparation) may include α2,3-sialylation in an amount which is from 65 to 85% of the total sialylation, for example from 70 to 80% of the total sialylation, for example from 71 to 79% of the total sialylation. The rFSH (or rFSH preparation) of the invention may have 50% or less of the total sialylation being α2,6-sialylation. For example 40, 30, 20, 10, 5% or less of the total sialylation may be α2,6-sialylation. The rFSH (or rFSH preparation) may include α2,6-sialylation in an amount which is from 15 to 35% of the total sialylation, for example from 20 to 30% of the total sialylation, for example from 21 to 29% of the total sialylation. The rFSH (or rFSH preparation) of the invention may have 5% or less of the total sialylation being α2,8-sialylation. For example 2.5% or less of the total sialylation may be α2,8-sialylation. The rFSH (or rFSH preparation) may include α2,8-sialylation in an amount which is from 0.1 to 4% of the total sialylation, for example from 0.5 to 3% of the total sialylation, for example from 0.5 to 2.5% of the total sialylation, By sialylation it is meant the amount of sialic residues present on the FSH carbohydrate structures. α2,3-sialylation means sialylation at the 2,3 position (as is well known in the art) and α2,6 sialylation at the 2,6 position (also well known in the art). Thus "% of the total sialylation may be a 2,3 sialylation" refers to the % of the total number of sialic acid residues present in the FSH which are sialylated in the 2,3 position. The term "% of the total sialylation being α2,6-sialylation" refers to the % of the total number of sialic acid residues present in the FSH which are sialylated in the 2,6 position.

The rFSH (or rFSH preparation) according to the invention may have a sialic acid content (amount of sialylation per FSH molecule) of (based on the mass of protein, rather than the mass of protein plus carbohydrate) of 6% or greater (e.g. between 6% and 15%, e.g. between 7% and 13%, e.g. between 8% and 12%, e.g. between 11% and 15%, e.g. between 12% and 14%) by mass.

Recombinant FSH expressed in Chinese hamster ovary (CHO) cells includes exclusively a 2, 3 sialylation (Kagawa et al, 1988, Takeuchi et al. 1988, Svensson et al. 1990).

The rFSH of the invention may be produced or expressed in a human cell line. This may simplify (and render more efficient) the production method because manipulation and control of e.g. the cell growth medium to retain sialylation may be less critical than with known processes. The method may also be more efficient because there is little basic rFSH produced than in production of known rFSH products; more acidic rFSH is produced and separation/removal of basic FSH is less problematic. The rFSH may be produced or expressed in a PER.C6® cell line (European Collection of Cell Cultures (ECACC) deposit number 96022940), a PER.C6® derived cell line or a modified PER.C6® cell line. The cell line may be modified using α2,3-sialyltransferase. The cell line may be modified using α2,6-sialyltransferase. Alternatively or additionally, the rFSH may include α2,6-linked sialic acids (α2,6 sialylation) provided by endogenous sialyl transferase activity [of the cell line].

The rFSH may be produced using α2,3- and/or α2,6-sialyltransferase. The rFSH may be produced using α2,3-sialyltransferase. The rFSH may include α2,6-linked sialic acids (α2,6 sialylation) provided by endogenous sialyl transferase activity.

According to the present invention in a further aspect there is provided a method of production of rFSH and/or an rFSH preparation as described herein (according to aspects of the invention) comprising the step of producing or expressing the rFSH in a human cell line, for example a PER.C6® cell line, a PER.C6® derived cell line or a modified PER.C6® cell line, for example a cell line which has been modified using α2,3-sialyltransferase.

The rFSH structure contains glycan moieties. Branching can occur with the result that the glycan may have 1, 2, 3, 4 or more terminal sugar residues or "antennae", as is well known in the art. The rFSH of the invention may have glycans with sialylation presence on mono-antennary and/or di-antennary and/or tri-antennary and/or tetra-antennary structures. The rFSH may preferably include mono-sialylated, di-sialylated, tri-sialylated and tetra-sialylated glycan structures with relative amounts as follows: 9-15% mono-sialylated; 27-30% di-sialylated; 30-36% tri-sialylated and 25-29% tetra-sialylated (e.g. as shown by WAX analysis of charged glycans, as set out in Example 8 c).

According to the present invention in a further aspect there is provided rFSH produced (e.g. expressed) in a human cell line. The rFSH may include α2,3- and α2,6-sialylation. The rFSH may be produced or expressed in a PER.C6® cell line, a PER.C6® derived cell line or a modified PER.C6® cell line. The cell line may be modified using α2,3-sialyltransferase. The cell line may be modified using α2,6-sialyltransferase. Alternatively or additionally, the rFSH may include α2,6-linked sialic acids (α2,6 sialylation) provided by endogenous sialyl transferase activity [of the cell line]. The rFSH (or rFSH preparation) may have 10% or more of the total sialylation being α2,3-sialylation, for example 65-85% of the total sialylation may be α2,3-sialylation. The rFSH (or rFSH preparation) of the invention may have 50% or less of the total sialylation being α2,6-sialylation, for example 15-35% of the total sialylation may be α2,6-sialylation. The rFSH (or rFSH preparation) of the invention may have 5% or less of the total sialylation being α2,8-sialylation, for example 0.5-4% of the total sialylation may be α2,8-sialylation. The rFSH may have a sialic acid content [expressed in terms of a ratio of moles of sialic acid to moles of protein] of 6 mol/mol or greater, for example between 6 mol/mol and 15 mol/mol.

According to the present invention in a further aspect there is provided a pharmaceutical composition comprising rFSH including α2,3-sialylation and α2,6-sialylation (e.g. as set out above). The pharmaceutical composition may further comprise hCG and/or LH.

hCG can be obtained by any means known in the art. hCG as used herein includes human-derived and recombinant hCG. Human-derived hCG can be purified from any appropriate source (e.g. urine, and placenta) by any method known in the art. Methods of expressing and purifying recombinant hCG are well known in the art.

LH can be obtained by any means known in the art. LH, as used herein, includes human-derived and recombinant LH. Human-derived LH can be purified from any appropriate source (e.g. urine) by any method known in the art. Methods of expressing and purifying recombinant LH are known in the art.

The pharmaceutical composition may be for the treatment of infertility, e.g. for use in e.g. assisted reproductive technologies (ART), ovulation induction or intrauterine insemination (IUI). The pharmaceutical composition may be used, for example, in medical indications where known FSH preparations are used. The present invention also provides the use of rFSH and/or an rFSH preparation described herein (according to aspects of the invention) for, or in the manufacture of a medicament for, the treatment of infertility. The pharmaceutical compositions of the present invention can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

The compositions of the present invention also can contain additives such as but not limited to preservatives, wetting agents, emulsifying agents, and dispersing agents. Antibacterial and antifungal agents can be included to prevent growth of microbes and includes, for example, paraben, chlorobutanol, phenol, sorbic acid, and the like. Furthermore, it may be desirable to include isotonic agents such as sugars, sodium chloride, and the like.

In some cases, to effect prolonged action it is desirable to slow the absorption of FSH (and other active ingredients, if present) from subcutaneous or intramuscular injection. This can be accomplished by the use of a liquid suspension of crystalline or amorphous material with poor water solubility. The rate of absorption of FSH then depends upon its rate of dissolution which, in turn, can depend upon crystal size and crystalline form. Alternatively, delayed absorption of a parenterally administered FSH combination form is accomplished by dissolving or suspending the FSH combination in an oil vehicle.

Injectable depot forms can be made by forming microencapsule matrices of the FSH (and other agents, if present) in biodegradable polymers such as polylactide-polyglycolide. Depending upon the ratio of FSH to polymer and the nature of the particular polymer employed, the rate of FSH release can be controlled. Examples of other biodegradable polymers include polyvinylpyrrolidone, poly(orthoesters), poly(anhydrides) etc. Depot injectable formulations are also prepared by entrapping the FSH in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

Injectable formulations can be supplied as a product having pharmaceutical compositions containing FSH (optionally with hCG, LH etc.) If there is more than one active ingredient (i.e. FSH and e.g. hCG or LH) these may be suitable for administration separately or together. If administered separately, administration can be sequential. The product can be supplied in any appropriate package. For example, a product can contain a number of pre-filled syringes containing either FSH, hCG, or a combination of both FSH and hCG, the syringes packaged in a blister package or other means to maintain sterility. A product can optionally contain instructions for using the FSH and hCG formulations.

The pH and exact concentration of the various components of the pharmaceutical composition are adjusted in accordance with routine practice in this field. See GOODMAN and GILMAN's THE PHARMACOLOGICAL BASIS FOR THERAPEUTICES, 7$^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

The present invention will now be described in more detail with reference to the following Examples and to the attached drawings.

Sequence Selection
Human FSH

The coding region of the gene for the FSH alpha polypeptide was used to according to Fiddes and Goodman. (1981). The sequence is banked as AH007338 and at the time of construction there were no other variants of this protein sequence. The nucleotide sequence is referred herein as SEQ ID NO:1.

The coding region of the gene for FSH beta polypeptide was used according to Keene et al (1989). The sequence is banked as NM_000510 and at the time of construction there were no other variants of this protein sequence. The sequence is referred herein as SEQ ID NO:2.

Sialyltransferase
α2,3-Sialyltransferase

The coding region of the gene for beta-galactoside alpha-2,3-sialyltransferase 4 (α2,3-sialyltransferase, ST3GAL4) was used according to Kitagawa and Paulson (1994). The nucleotide sequence is banked as L23767 and referred herein as SEQ ID NO:3.

α2,6-Sialyltransferase

The coding region of the gene for beta-galactosamide alpha-2,6-sialyltransferase 1 (α2,6-sialyltransferase, ST6GAL1) was used according to Grundmann et al. (1990). The nucleotide sequence is banked as NM_003032 and referred herein as SEQ ID NO:4.

Plasmids

Figure 1:
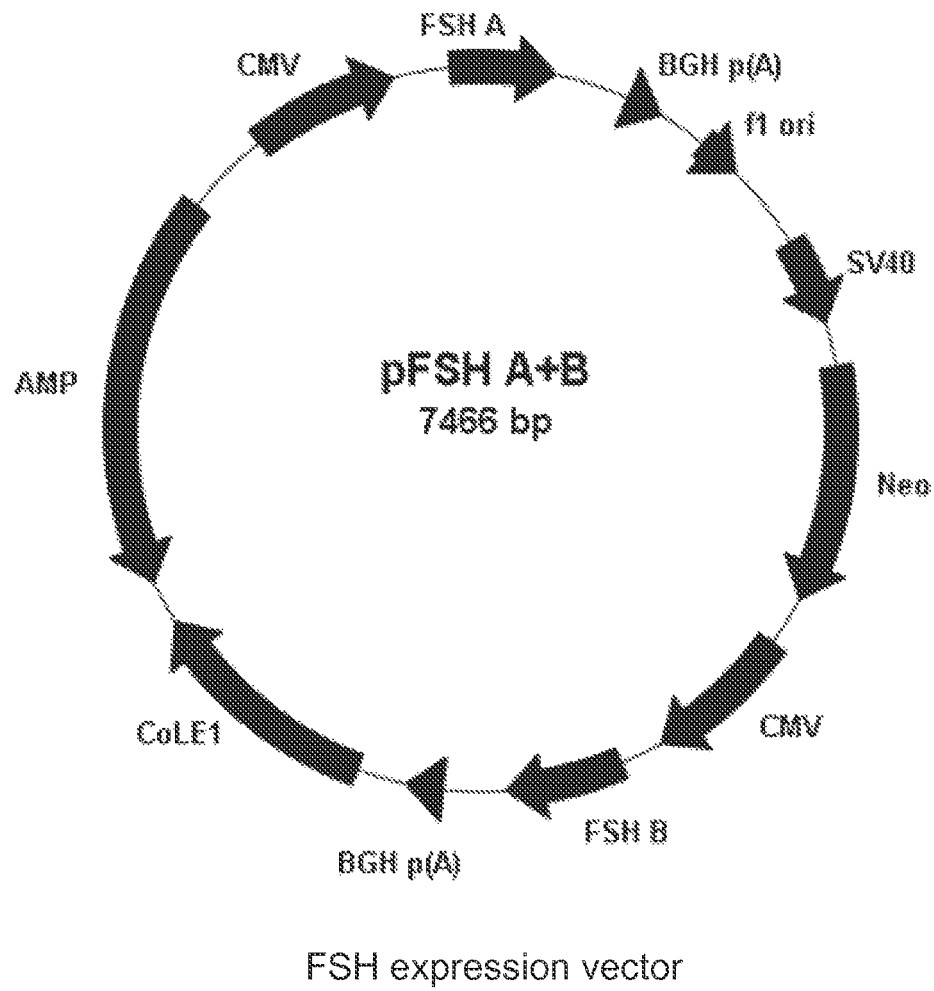
FIG. 1 is a plasmid map of the pFSHalpha/beta expression vector.
Figure 2:
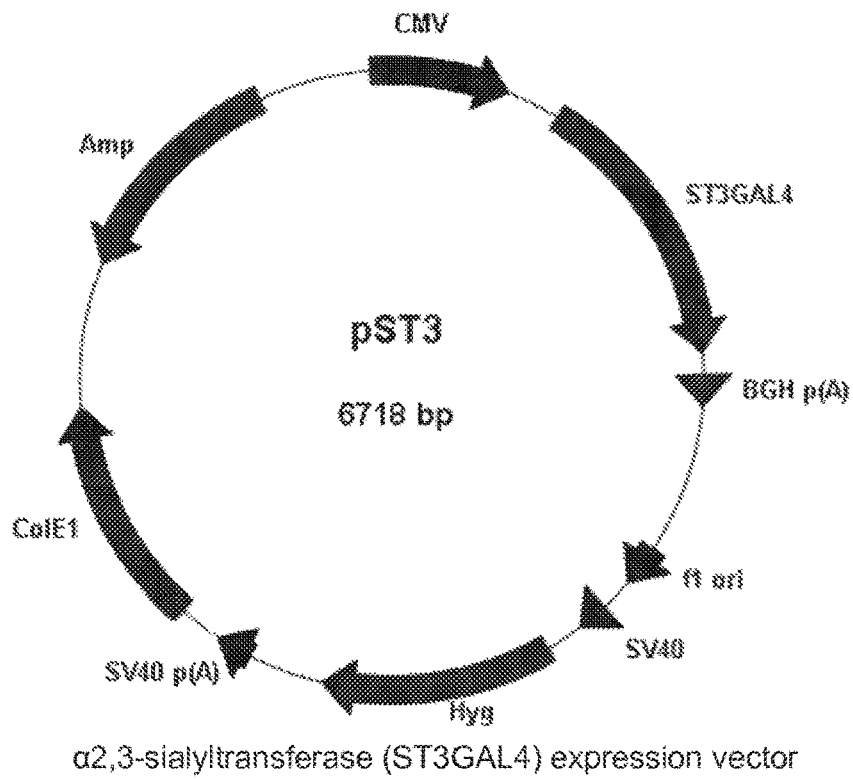
FIG. 2 is a representation of the α2,3-sialyltransferase (ST3GAL4) expression vector.
Figure 3:
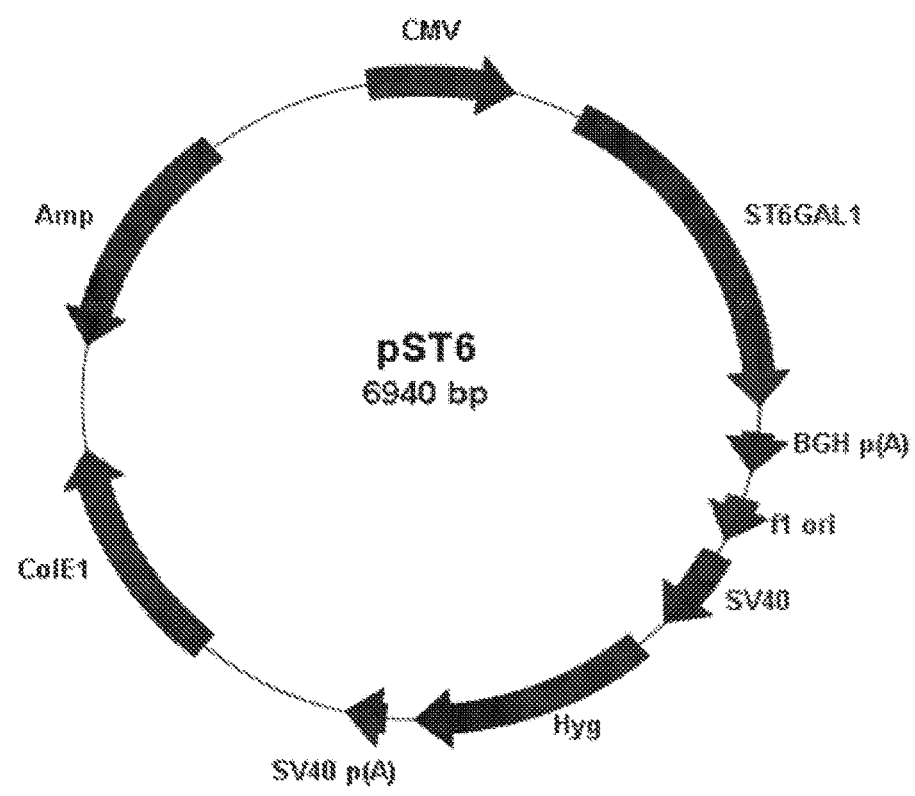
FIG. 3 is a representation of the α2,6-sialyltransferase (ST6GAL1) expression vector.

FIGS. 1, 2 and 3 are plasmid maps of the pFSHalpha/beta, pST3 and pST6 expression vectors described in greater detail below. CMV=Cytomegalovirus promoter, BGHp(A)=Bovine Growth Hormone poly-adenylation sequence, fl ori=fl origin of replication, SV40=Simian Virus 40 promoter, Neo=Neomycin resistance marker, Hyg=Hygromycin resistance marker, SV40 p(A)=Simian Virus 40 poly-adenylation sequence, FSH A=Follicle stimulating hormone alpha polypeptide, FSH B=Follicle stimulating hormone beta polypeptide, ST3GAL4=α2,3-sialyltransferase, ST6GAL1=α2,6-sialyltransferase, ColEI=ColEI origin of replication, Amp=ampicillin resistance marker.

EXAMPLES

Example 1 Construction of the FSH Expression Vector

The coding sequence of FSH alpha polypeptide (AH007338, SEQ ID NO:1) and FSH beta polypeptide (NM_003032, SEQ ID 2) were amplified by PCR using the primer combinations FSHa-fw and FSHa-rev and FSHb-fw and FSHb-rec respectively.

FSHa-fw
(SEQ ID NO: 9)
5'-CCAGGATCCGCCACCATGGATTACTACAGAAAAATATGC-3'

FSHa-rev
(SEQ ID NO: 10)
5'-GGATGGCTAGCTTAAGATTTGTGATAATAAC-3'

FSHb-fw
(SEQ ID NO: 11)
5'-CCAGGCGCGCCACCATGAAGACACTCCAGTTTTTC-3'

FSHb-rev
(SEQ ID NO: 12)
5'-CCGGGTTAACTTATTATTCTTTCATTTCACCAAAGG-3'

The resulting amplified FSH beta DNA was digested with the restriction enzymes AscI and HpaI and inserted into the AscI and HpaI sites on the CMV driven mammalian expression vector carrying a neomycin selection marker. Similarly the FSH alpha DNA was digested with BamHI and NheI and inserted into the sites BamHI and NheI on the expression vector already containing the FSH beta polypeptide DNA.

The vector DNA was used to transform the DH5a strain of E. coli. Sixty colonies were picked for amplification and fifty seven contained the vector containing both FSH alpha and beta. Twenty of these were selected for sequencing and all contained the correct sequences according to SEQ ID NO:1 and SEQ ID NO:2. Plasm id pFSH A+B #17 was selected for transfection (FIG. 1).

Example 2 Construction of the ST3 expression vector The coding sequence of beta-galactoside alpha-2,3-sialyltransferase 4 (ST3, L23767, SEQ ID NO:3) was amplified by PCR using the primer combination 2,3STfw and 2,3STrev.

2,3STfw
(SEQ ID NO: 13)
5'-CCAGGATCCGCCACCATGTGTCCTGCAGGCTGGAAGC-3'

2,3STrev
(SEQ ID NO: 14)
5'-TTTTTTTCTTAAGTCAGAAGGACGTGAGGTTCTTG-3'

The resulting amplified ST3 DNA was digested with the restriction enzymes BamHI and AR and inserted into the BamHI and AflII sites on the CMV driven mammalian expression vector carrying a hygromycin resistance marker. The vector was amplified as previously described and sequenced. Clone pST3 #1 (FIG. 2) contained the correct sequence according to SEQ ID NO:3 and was selected for transfection.

Example 3 Construction of the ST6 Expression Vector

The coding sequence of beta-galactosamide alpha-2,6-sialyltransferase 1 (ST6, NM_003032, SEQ ID NO:4) was amplified by PCR using the primer combination 2,6STfw and 2,6STrev.

2,6STfw
(SEQ ID NO: 15)
5'-CCAGGATCCGCCACCATGATTCACACCAACCTGAAG-3'

2,6STrev
(SEQ ID NO: 16)
5'-TTTTTTTCTTAAGTTAGCAGTGAATGGTCCGG-3'

The resulting amplified ST6 DNA was digested with the restriction enzymes BamHI and AR and inserted into the BamHI and AflII sites on the CMV driven mammalian expression vector carrying a hygromycin resistance marker. The vector was amplified as previously described and sequenced. Clone pST6 #11 (FIG. 3) contained the correct sequence according SEQ ID NO:4 and was selected for transfection.

Example 4 Stable Expression of pFSH A+B in PER.C6® Cells. Transfection Isolation and Screening of Clones PER.C6® clones producing FSH were generated by expressing both polypeptide chains of FSH from a single plasmid (see Example 1).

To obtain stable clones a liposome based transfection agent with the pFSH A+B construct. Stable clones were selected in VPRO supplemented with 10% FCS and containing G418. Three weeks after transfection G418 resistant clones grew out. A total of 250 clones were selected for isolation. The isolated clones were cultured in selection medium until 70-80% confluent. Supernatants were assayed for FSH protein content using an FSH selective ELISA and pharmacological activity at the FSH receptor in cloned cell line, using a cAMP accumulation assay. Clones (98) expressing functional protein were progressed for culture expansion to 24 well, 6 well and T80 flasks.

Studies to determine productivity and quality of the material from seven clones were initiated in T80 flasks to generate sufficient material. Cells were cultured in supplemented media as previously described for 7 days and the supernatant harvested. Productivity was determined using the FSH selective ELISA. The isoelectric profile of the material was determined (Example 6). Representative samples are shown in FIG. 4. The information from the IEF was used to select clones for metabolic clearance rate analysis (Example 9). Clones (005, 104, 179, 223, 144) with sufficient productivity and quality were selected for sialyl-transferase engineering.

Example 5 Level of Sialylation is Increased in Cells that Over Express α2,3- or α2,6-Sialyltransferase. Stable Expression of pST3 or pST6 in FSH Expressing PER.C6® Cells; Transfection Isolation and Screening of Clones PER.C6® clones producing highly sialylated FSH were generated by expressing α2,3 sialyltransferase or α2,6 sialyltransferase from separate plasmids (see Examples 2 and 3) in PER.C6® cells already expressing both polypeptide chains of FSH (see Example 4). Four clones produced from PER.C6® cells as set out in Example 4 were selected for their characteristics including productivity, good growth profile, production of functional protein, and produced FSH which included some sialylation.

Stable clones were generated as previously described in Example 4. A total of 202 clones from the α2,3-sialyltransferase program and 210 clones from the α2,6-sialyltransferase program were isolated, expanded and assayed. The final clone number for the α2,3-study was 12 and 30 for the α2,6-study.

The α2,3-sialyltransferase clones were adapted to serum free media and suspension conditions.

As before clones were assayed using a FSH selective ELISA, functional response in an FSH receptor cell line, IEF (Example 6), metabolic clearance rate (Example 9) and Steelman Pohley analysis (Example 10). Results were compared to a commercially available recombinant FSH (GO-NAL-F®, Serono) and the parental FSH PER.C6® cell lines. Representative samples are shown in FIG. 5. Some clones did not demonstrate an increase in sialylation but it can be seen that FSH produced by most of the clones has significantly improved sialylation (i.e. on average more FSH isoforms with high numbers of sialic acids) compared to FSH expressed without α2,3- or α2,6-sialyltransferase.

In conclusion, expression of FSH together with sialyl-transferase in PER.C6® cells results in increased levels of sialylated FSH compared to cells expressing FSH only.

Example 6 Analysis of the pI of PER.C6® Cell Produced FSH Isoforms by Isoelectric Focusing Electrophoresis is defined as the transport of charged molecules through a solvent by an electrical field. The mobility of a biological molecule through an electric field will depend on the field strength, net charge on the molecule, size and shape of the molecule, ionic strength and properties of the medium through which the molecules migrate.

Isoelectric focusing (IEF) is an electrophoretic technique for the separation of proteins based on their pI. The pI is the pH at which a protein has no net charge and will not migrate in an electric field. The sialic acid content of the FSH isoforms subtly alters the pI point for each isoform, which can be exploited using this technique to visualise the FSH isoforms produced in PER.C6® cells from each clone.

The isoelectric points of the FSH isoforms produced in PER.C6® cell culture supernatants were analysed using isoelectric focusing. Cell culture media from PER.C6® cell FSH clones was produced as described in Example 4 and 5.

FSH samples produced in PER.C6® cells were separated on NOVEX® IEF Gels containing 5% polyacrylamide under native conditions on a pH 3.0-7.0 gradient in an ampholyte solution pH 3.0-7.0.

Proteins were transferred onto supported nitrocellulose and visualised using a primary anti-FSHα monoclonal antibody, secondary anti-mouse IgG alkaline phosphatase conjugated antibody and 5-bromo-4-chloro-3-indolyl-phosphate (BCIP) and nitro blue tetrazolium (NBT) reagent to visualise the bands.

As indicated in FIGS. 4 and 5, the bands represent isoforms of FSH containing different numbers of sialic acid molecules.

FIG. 4 is a representation of an isoelectric focusing gel showing the results of recombinant FSH produced by PER.C6® cells stably expressing FSH. Cell culture supernatants were separated under native conditions on a pH 3.0-7.0 gradient. Clones containing less acidic isoforms were discarded. Clone 005 is representative of the five clones taken forward for sialytransferase engineering.

FIG. 5 is a representation of an isoelectric focusing gel that shows clones analyzed by isoelectric focusing of recombinant FSH produced by PER.C6® cells stably expressing FSH after engineering with α2,3- or α2,6-sialyltransferase. Cell culture supernatants were separated under native conditions on a pH 3.0-7.0 gradient. Clone 005 is the parental PER.C6® FSH cell line. Clones displaying basic or mixed profiles (designated by *) were discontinued. The remaining clones demonstrate successful engineering with a sialyl-transferase to increase the number of sialic acid molecules on FSH.

Using this method clones producing FSH isoforms with a higher number of sialic acid molecules were identified. Engineering with α2,3- or α2,6-sialyltransferase resulted in clones with more sialic acid and a lower pI.

Example 7 Analysis of the Sialic Acid Linkages of PER.C6® Cell Produced FSH

Glycoconjugates were analysed using a lectin based glycan differentiation method. With this method glycoproteins and glycoconjugates bound to nitrocellulose can be characterized. Lectins selectively recognize a particular moiety, for example α2,3 linked sialic acid. The lectins applied are conjugated with the steroid hapten digoxigenin which enables immunological detection of the bound lectins.

Purified FSH produced from a PER.C6® cell parental clone (no additional sialyltransferase), a α2,3-sialyltransferase engineered clone and a α2,6-sialyltransferase engineered clone were separated using standard SDS-PAGE techniques. A commercially available recombinant FSH (GONAL-F®, Serono) was used as a standard.

Sialic acid was analysed using the DIG Glycan Differentiation Kit (Cat. No. 11 210 238 001, Roche) according to the manufacturers instructions. Positive reactions with *Sambucus nigra* agglutinin (SNA) indicated terminally linked (2-6) sialic acid. Positive reactions with *Maackia amurensis* agglutinin II (MAA): indicated terminally linked (α2-3) sialic acid In summary the parental clone 005 contained low levels of both α2,3- and α2,6-sialic acid. The clones engineered with α2,3-sialyltransferase contained high levels of α2,3-sialic acid linkages and low levels of α2,6-sialic acid linkages. Clones engineered with α2,6-sialyltransferase contained high levels of α2,6-sialic acid linkages and low levels of α2,3-sialic acid linkages. The standard control GONAL-F® FSH only contains α2,3-sialic acid linkages. This is consistent with what is known about recombinant proteins produced in Chinese Hamster ovary (CHO) cells (Kagawa et al, 1988, Takeuchi et al, 1988, Svensson et al., 1990).

Figure 6A:
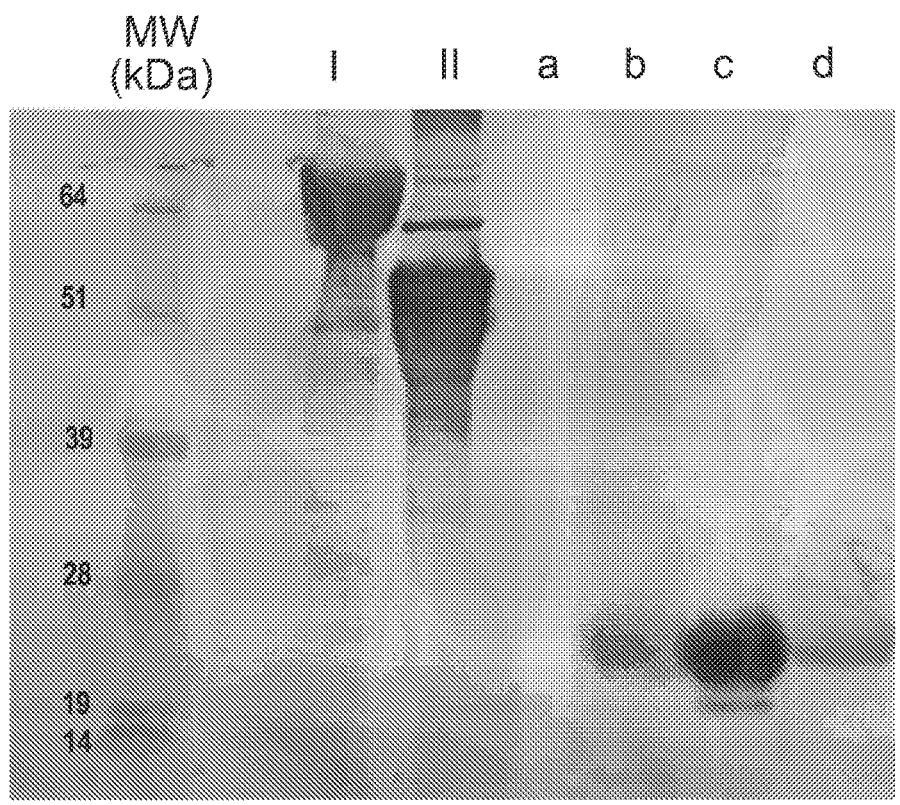
FIGS. 6A and 6B are representations of SDS PAGE gels that show the analysis of sialic acid linkages of PER.C6® FSH.
Figure 6B:
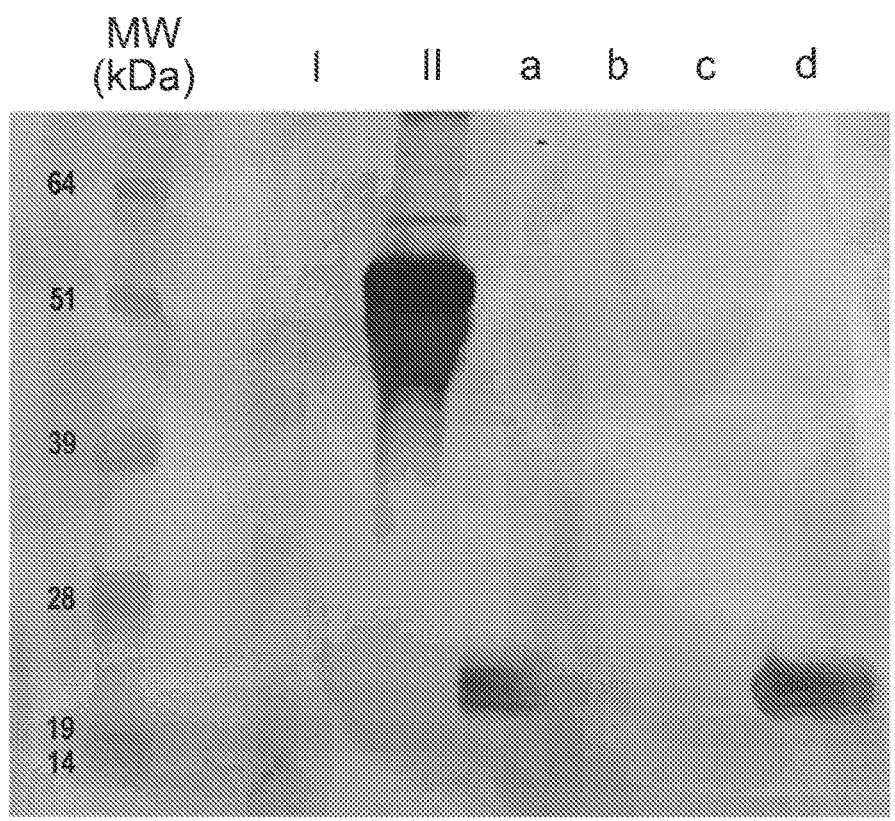

FIGS. 6A and 6B are representations of SDS PAGE gels that show the analysis of sialic acid linkages of PER.C6e FSH. Purified FSH prepared in PER.C6® cells was separated by SDS PAGE on duplicate gels, transferred to nitrocellulose and visualised using the DIG Glycan Differentiation Kit (Cat. No. 11 210 238 001, Roche) according to the manufacturer's instructions. Positive reactions with Sam bucus nigra agglutinin (SNA) indicated terminally linked (2-6) sialic acid (FIG. 6A). Positive reactions with *Maackia amurensis* agglutinin (MAA): indicated terminally linked (2-3) sialic acid (FIG. 6B). The lanes on the gel are as follows: Lane I manufacturers control containing α2,6 linkages only. Lane II manufacturers control containing α2,6 and α2,3 linkages. Sample a. Commercial CHO cell derived recombinant FSH (GONAL-F®, Serono). Sample b, Recombinant FSH produced in parental PER.C6® cells without sialyl-transferase engineering. Sample c. Recombinant FSH produced in PER.C6e cells with α2,6-sialyltransferase engineering. Sample d. Recombinant FSH produced in PER.C6® cells with α2,3-sialyltransferase engineering.

In conclusion, engineering of FSH producing PER.C6® cells with α2,3- or α2,6-sialyltransferase successfully increased the number of sialic acid molecules conjugated to the FSH in the sample.

Example 8a Quantification of Total Sialic Acid

Sialic acid is a protein-bound carbohydrate considered to be a mono-saccharide and occurs in combination with other mono-saccharides like galactose, mannose, glucosamine, galactosamine and fucose.

The total sialic acid on purified rFSH (Example 11) was measured using an enzymatic sialic acid quantification kit according to the manufacturers protocol (Sigma, Sialic-Q). In short N-acetylneuraminic acid aldolase catalyses sialic acid to N-acetylmannoasine and pyruvic acid. The pyruvic acid can be reduced to lactic acid by β-NADH and lactic dehydrogenase. B-NADH oxidation can be accurately measured spectrophotometrically.

Protein concentration was measured in microtiter plates using a commercial bicinchoninic acid (BCA) assay kit (Sigma, B 9643) based on the Lowry method (Lowry et al, 1951).

The total sialic acid content of FSH produced in PER.C6® cells was measured and found to be greater than 6 mol/mol.

Example 8b Quantification of Relative Amounts of α2,3, α2,6 and α2,8 Sialic Acid The relative percentage amounts of α2,3, α2,6 and α2,8 sialic acid on purified rFSH (Example 11) were measured using known techniques.

Each sample of rFSH was immobilized (gel block), washed, reduced, alkylated and digested with PNGase F overnight. The N-glycans were then extracted and processed. N-glycans for NP-HPLC and WAX-HPLC analysis were labelled with the fluorophore 2AB as detailed in Royle et al. The N-glycans were run on normal phase (NP) HPLC on a TSK amide column (as detailed in Royle et al) with retention times expressed in glucose units (GU).

Samples of the extracted, pooled, glycans (extracted as above) were digested with different sialidases to determine the linkages. NAN 1 (recombinant sialidase) releases α2,3 linked non-reducing terminal sialic acids (NeuNAc and NeuNGc), ABS (*Arthrobacter ureafaciens* sialidase) releases α2,3, α2,6 and α2,8 linked non-reducing terminal sialic acids (NeuNAc and NeuNGc). Samples were analysed by NP-HPLC, to allow comparison of the undigested sample with that digested with NAN1 and that digested with ABS. Comparison of the three NP-HPLC traces (undigested, NAN1 digested, ABS digested) shows that digestion with ABS and NAN1 give different results. This indicates that the samples have sialic acids with α2,3, α2,6 and α2,8 linkages. The relative percentages were calculated from structures present in the undigested glycan pools and were found to be in the ranges 65%-85% (e.g. 77.75%) for α2,3 sialylation; 15 to 35% (e.g. 21.46%) for α2,6 sialylation; and 0.1 to 3% for α2,8 sialylation.

Example 8c Quantification of Relative Amounts Mono, Di, Tri and Tetra Antennary Sialylated Structures The relative percentage amounts of mono, di, tri and tetra sialylated structures on glycans extracted from purified rFSH (Example 11) were measured using known techniques.

Each sample of rFSH was immobilized (gel block), washed, reduced, alkylated and digested with PNGase F overnight. The N-glycans were then extracted and processed. N-glycans for NP-HPLC and WAX-HPLC analysis were labelled with the fluorophore 2AB as detailed in Royle et al.

Weak anion exchange (WAX) HPLC to separate the N-glycans by charge (Example 8b) was carried out as set out in Royle et al, with a Fetuin N-glycan standard as reference. Glycans were eluted according to the number of sialic acids they contained. All samples included mono (1S), di(2S), tri(3S) and tetra(4S) sialylated structures. The relative amounts of sialylated structures were found to be in the following ratios (1S:2S:4S:4S): 9-15%: 27-30%: 30-36%: 25-29% (for example 10.24:28.65:35.49:25.62).

Example 9 Determination of the Metabolic Clearance Rates of rFSH

To determine the metabolic clearance rate (MCR) of FSH samples produced in PER.C6® cells, conscious female rats (3 animals per clone) were injected into the tail vein at time zero with a bolus of rFSH (1-10 μg/rat, based on ELISA quantification of samples, DRG EIA 1288). Blood samples (400 pl) were taken from the tip of the tail at 1, 2, 4, 8, 12, 24 and 32 hours after test sample injection. Serum was collected by centrifugation and assayed for FSH content by ELISA (DRG EIA 1288)

The asialoglycoprotein receptor (ASGP-R) recognizes desialyated (galactose-terminated) glycoproteins such as asialofetuin (ASF). (Pricer and Ashwell, 1971. Van Lenten and Ashwell, 1972). The ASGP receptor and the bound desialyated glycoprotein are internalized into the cell where the receptor is recycled and the ligand is degraded (Regoeczi et al, 1978, Steer and Ashwell, 1980).

To investigate if FSH material produced in PER.C6® cells was cleared via this mechanism, the ASGP-R was saturated with asialofetuin. The metabolic clearance rate of parental, α2,6 or α2,3-sialyltransferase engineered material was determined as described with co administration of a minimum 7500-fold molar excess of asialofetuin to saturate the ASGP-R for 1-2 h.

Figure 10:
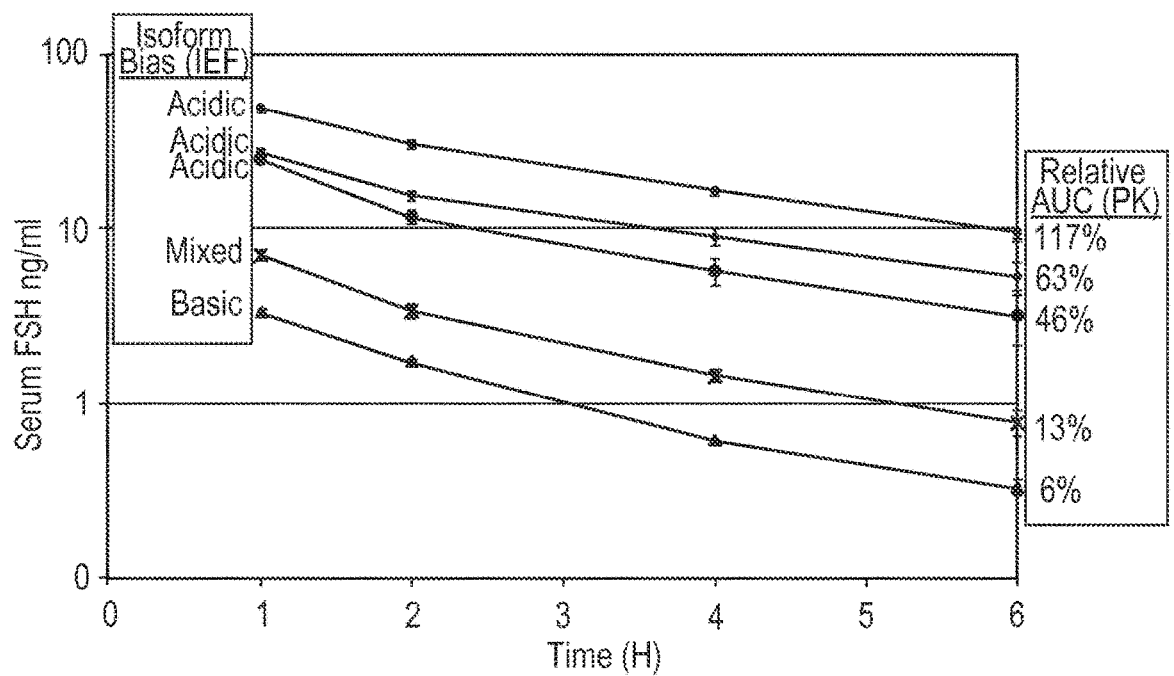
FIG. 10 is a graph that shows MCRs of α2,3-sialytransferase engineered PER.C6® FSH samples.

The material produced by the parental PER.C6® cell FSH clones contained some longer MCR material but a high percentage was cleared quickly (FIG. 7). The lead clone 005 which contained the most sialylated material was engineered using α2,6- or α2,3-sialyltransferase (Example 5). Although the clones engineered with α2,6-sialyltransferase demonstrated increased sialylation (FIG. 5) there was no improvement in the MCR (FIG. 7). Blockade of the ASGR restored the MCR of the α2,6 material to that of the standard demonstrating that even with increased α2,6 linkages the material is cleared quickly (FIG. 8). Engineering with α2,3-sialyltransferase resulted in clones with comparable MCR to the standard (FIG. 9) and varying sialic content was consistent with what is known for the isoforms of FSH (FIG. 10).

FIG. 7 is a graph that shows Metabolic clearance rates of PER.C6® cell produced FSH samples. Female rats (3 animals per clone) were injected into the tail vein at time zero with a bolus of rFSH (1-10 μg/rat). Blood samples collected over time were assayed for FSH content by ELISA.

FIG. 8 is a graph that shows MCRs of α2,6-sialytransferase engineered PER.C6® FSH samples. Female rats (3 animals per clone) were injected into the tail vein at time zero with a bolus of rFSH (1-10 μg/rat). Blood samples collected over time were assayed for FSH content by ELISA.

FIG. 9 is a graph that shows MCRs of α2,6-sialytransferase engineered PER.C6® FSH samples with co administration of a 7500-fold molar excess of asialofetuin to saturate the ASGP-R for 1-2 h.

FIG. 10 is a graph that shows MCRs of α2,3-sialytransferase engineered PER.C6® FSH samples. Samples were chosen for their sialic acid content based on their IEF profile.

Example 10 Steelman-Pohley In Vivo Assay

To demonstrate increasing sialic acid content on FSH results in an increased biological effect, the increase in ovarian weights in rats by highly sialylated FSH such as produced in Example 5 was examined.

The increase in ovarian weights due to the rFSH produced in PER.C6® cell clones were analysed according to the method of Steelman and Pohley (1953). rFSH produced in PER.C6® cells from filtered cell media samples was quantified by ELISA (DRG,EIA-1288). The samples (PER.C6® cell produced rFSH) and standards (GONAL-F® rFSH) were tested at five different doses (3 animals/dose). GONAL-F® was dosed at 50, 100, 200, 400, and 800 ng/rat. The sample doses were calculated using their AUC values relative to GONAL-F®, typically 0.05-10 μg/rat.

Figure 11:
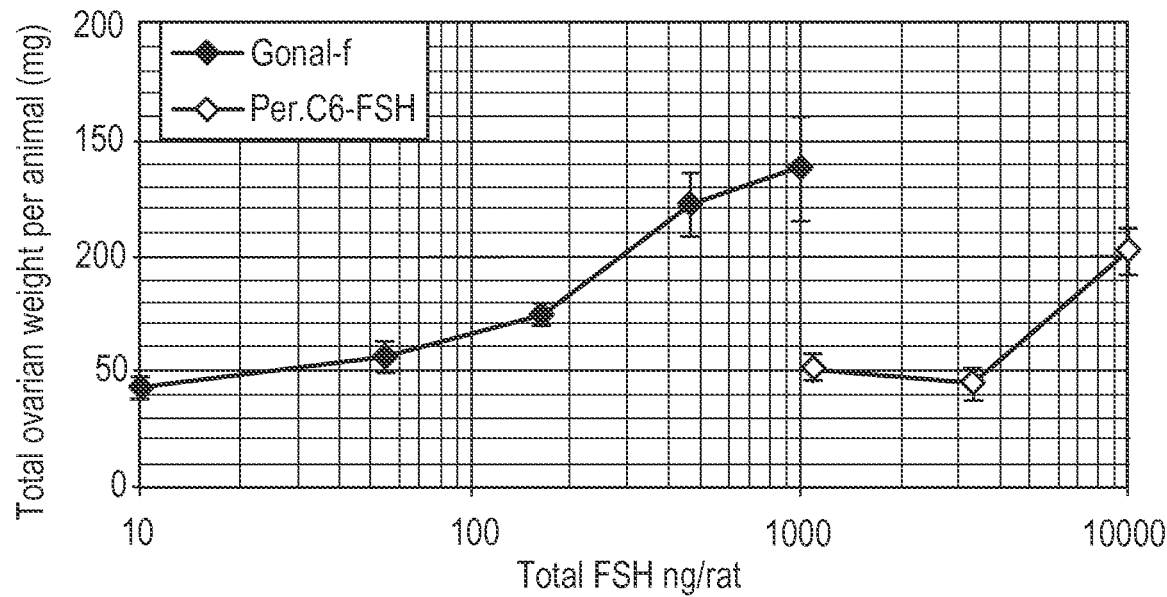
FIG. 11 is a graph that shows ovarian weight augmentation by PER.C6® rFSH clones of parental PER.C6® rFSH, according to the method of Steelman and Pohley (1953), Endocrinology, 53(6):604-616.

FIG. 11 is a graph that shows ovarian weight augmentation by parental PER.C6® cell produced rFSH, according to the method of Steelman and Pohley (1953), *Endocrinology*, 53(6):604-616. PER.C6® cell rFSH and standards (GONAL-F® rFSH) were tested at different doses (3 rats/dose).

Figure 12:
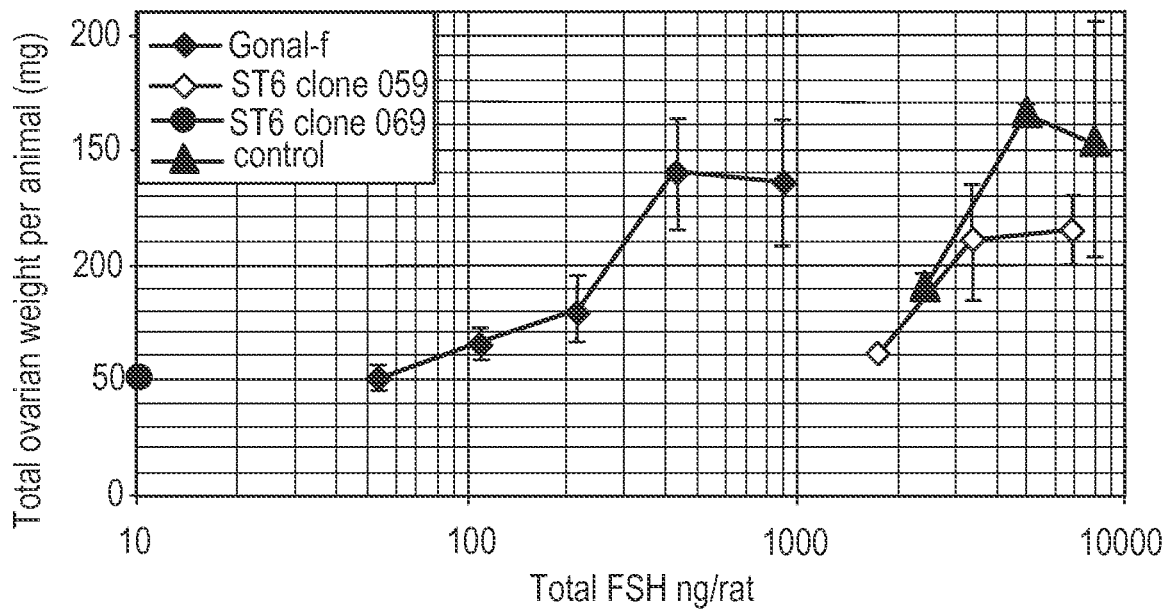
FIG. 12 is a graph that shows ovarian weight augmentation by PER.C6® rFSH clones of engineered (α2,6-sialyltransferase) PER.C6® rFSH.

FIG. 12 is a graph that shows ovarian weight augmentation by rFSH produced in PER.C6® cell clones engineered to produce α2,6-sialyltransferase. The engineered (α2,6-sialyltransferase) PER.C6® cell rFSH and standards (GONAL-F® rFSH) were tested at different doses (3 rats/dose).

Figure 13:
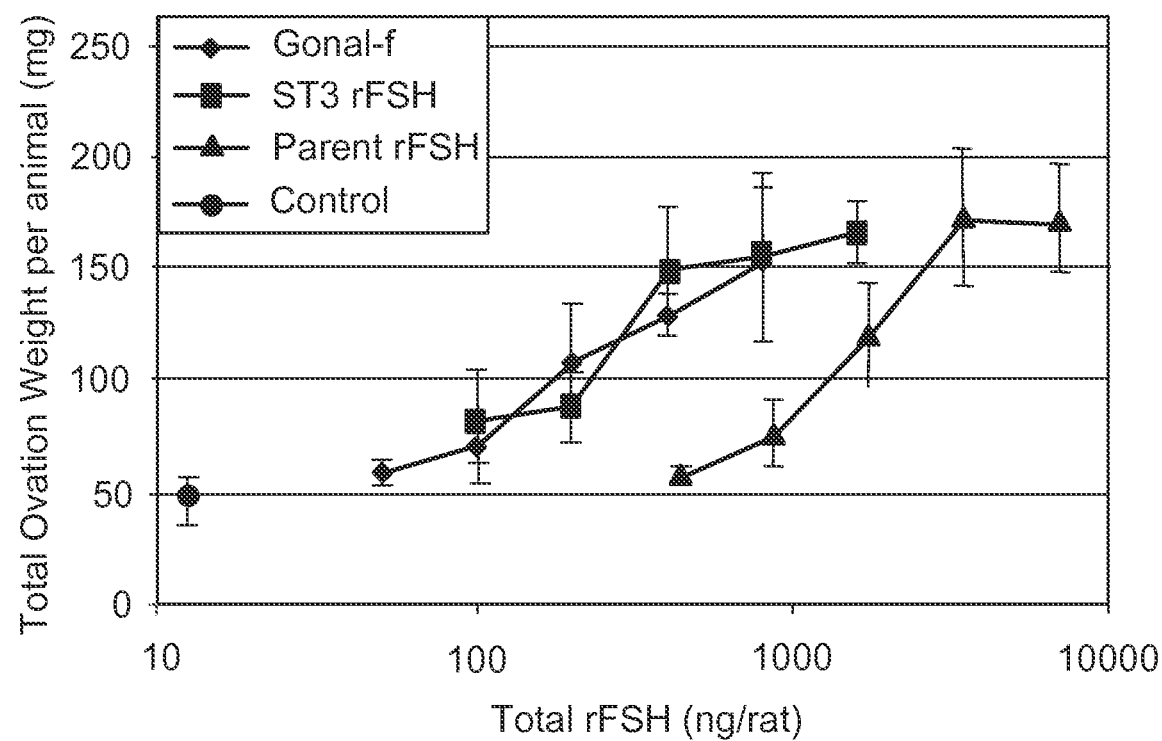
FIG. 13 is a graph that shows ovarian weight augmentation by PER.C6® rFSH clones of engineered (α2,3-sialyltransferase) PER.C6® rFSH.

FIG. 13 is a graph that shows ovarian weight augmentation by rFSH produced in PER.C6® cell clones engineered to produce α2,6-sialyltransferase PER.C6® cell clones engineered to produce α2,6-sialyltransferase PER.C6® cell clones engineered to produce α2,6-sialyltransferase. The engineered (α2,3-sialyltransferase) PER.C6® cell rFSH and standards (GONAL-F® rFSH) were tested at different doses (3 rats/dose).

In conclusion, the undersialylated material produced by the parental PER.C6® cell FSH clones (FIG. 11) was not as potent in the ovarian weight augmentation assay as the commercially available rFSH. Sialyltransferase engineering to add additional α2,6-linkages increased the sialic acid content but did not improve potency in the in vivo assay (FIG. 12). However, additional α2,3-linkages significantly improved potency (FIG. 13) and the two recombinant FSH preparations (PER.C6® cell and CHO-cell derived) display very similar profiles in this assay.

Example 11 Production and Purification Overview

A procedure was developed to produce FSH in PER.C6® cells that were cultured in suspension in serum free medium. The procedure is described below and was applied to several FSH-producing PER.C6® cell lines.

FSH from the parental clone 005, α2,3-clone 007 and α2,6 clone 059 was prepared using a using a modification of the method described by Lowry et al. (1976).

For the production of FSH in PER.C6® cells, the cell lines were adapted to a serum-free medium, i.e., EXCELL™ 525 (JRH Biosciences). The cells were first cultured to form a 70%-90% confluent monolayer in a T80 culture flask. On passage the cells were re-suspended in the serum free medium, EXCELL™ 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $>1 \times 10^6$ cells/ml, the cells were sub-cultured to a cell density of 0.2 or $0.3 \times 10^6$ cells/ml and further cultured in shaker flasks at 37° C., 5% $CO_2$ and 100 rpm.

For the production of FSH, the cells were transferred to a serum-free production medium, i.e., VPRO (JRH Biosciences), which supports the growth of PER.C6® cells to very high cell densities (usually $>10^7$ cells/ml in a batch culture). The cells were first cultured to $>1 \times 10^6$ cells/ml in EXCELL™ 525, then spun down for 5 min at 1000 rpm and subsequently suspended in VPRO medium+6 mM L-glutamine to a density of $1\times10^6$ cells/ml. The cells were then cultured in a shaker flask for 7-10 days at 37° C., 5% CO2 and 100 rpm. During this period, the cells grew to a density of >$10^7$ cells/ml. The culture medium was harvested after the cell viability started to decline. The cells were spun down for 5 min at 1000 rpm and the supernatant was used for the quantification and purification of FSH. The concentration of FSH was determined using ELISA (DRG EIA 1288).

Thereafter, purification of FSH was carried out using a modification of the method described by Lowry et al. (1976). This was achieved by chromatography on DEAE cellulose, gel filtration on SEPHADEX® G100 adsorption chromatography on hydroxyapatite, and preparative polyacrylamide electrophoresis.

During all chromatographic procedures, the presence of immunoreactive FSH was confirmed by RIA (DRG EIA 1288) and IEF (Example 6).

REFERENCES

Andersen C Y, Westergaard L G, and van Wely M. (2004). FSH isoform composition of commercial gonadotrophin preparations: a neglected aspect? Reprod. Biomed. Online. 9(2), 231-236.

Arey B J, Stevis P E, Deecher D C, Shen E S, Frail D E, Negro-Vilar A, and Lopez F J. (1997) Induction of promiscuous G protein coupling of the follicle-stimulating hormone (FSH) receptor: a novel mechanism for transducing pleiotropic actions of FSH isoforms. Mol Endocrinol. 11(5), 517-526.

Baenziger J U and Green E D. (1988). Pituitary glycoprotein hormone oligosaccharides: structure, synthesis and function of the asparagine-linked oligosaccharides on lutropin, follitropin and thyrotropin. Biochim Biophys Acta. 947 (2), 287-306.

Bassett R M, and Driebergen R. (2005). Continued improvements in the quality and consistency of follitropin alfa, recombinant human FSH. Reprod Biomed Online. 10(2), 169-177.

Damián-Matsumura P, Zaga V, Maldonado A, Sánchez-Hernández C, Timossi C, and Ulloa-Aguirre A. (1999). Oestrogens regulate pituitary alpha2,3-sialyltransferase messenger ribonucleic acid levels in the female rat. J Mol Endocrinol. 23(2), 153-165.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Dalpathado D S, Irungu J, Go E P, Butnev V Y, Norton K, Bousfield G R, and Desaire H. (2006). Comparative glycomics of the glycoprotein follicle stimulating hormone: glycopeptide analysis of isolates from two mammalian species. Biochemistry. 45(28), 8665-8673.

Dias J A, Van Roey P. (2001). Structural biology of human follitropin and its receptor. Arch Med Res. 32(6), 510-519

Fiddes, J. C. and Goodman, H. M. (1979) Isolation, cloning and sequence analysis of the cDNA for the alpha-subunit of human chorionic gonadotropin. Nature, 281, 351-356.

Flack, M. R., Bennet, A. P., Froehlich, J. Anasti, J N and Nisula, B. (1994). Increased biological activity due to basic isoforms in recombinant human follicle-stimulating hormone produced in a human cell line. J. Clin. Endocrinol. Metab., 79, 756-760

Fox K M, Dias J A, and Van Roey P. (2001). Three-dimensional structure of human follicle-stimulating hormone. Mol Endocrinol. 15(3), 378-89

Grabenhorst E, Hoffmann A, Nimtz M, Zettlmeissl G, and Conradt H S. (1995). Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal (beta 1-4)GlcNAc(beta 1-2)Man(alpha 1-3)-branch of diantennary oligosaccharides from secreted recombinant beta-trace protein. Eur J Biochem. 232(3), 718-25.

Green E D and Baenziger J U. (1988). Asparagine-linked oligosaccharides on lutropin, follitropin, and thyrotropin. II. Distributions of sulfated and sialylated oligosaccharides on bovine, ovine, and human pituitary glycoprotein hormones. J Biol Chem. 263(1), 36-44.

Grundmann, U., Nerlich, C., Rein, T. and Zettlmeissl, G. (1990). Complete cDNA sequence encoding human beta-galactoside alpha-2,6-sialyltransferase. G Nucleic Acids Res. 18 (3), 667

Howles, C. M. (1996). Genetic engineering of human FSH (Gonal-F). Hum Reprod. Update, 2, 172-191.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Keene, J. L., Matzuk, M. M., Otani, T., Fauser, B, C, J, M., Galway, A. B., Hsueh, A. J. W. and Boime, I. (1989). Expression of Biologically active Human Follitropin in Chinese Hamster Ovary Cells. The Journal of Biological Chemistry, 264(9), 4769-4775.

Kitagawa, H. and Paulson, J. O. (1994) Cloning of a novel alpha 2,3-sialyltransferase that sialylates glycoprotein and glycolipid carbohydrate groups. J. Biol. Chem. 269(2), 1394-1401.

Lee E U, Roth J, and Paulson J C (1989) Alteration of terminal glycosylation sequences on N-linked oligosaccharides of Chinese hamster ovary cells by expression of beta-galactoside alpha 2,6-sialyltransferase. J Biol Chem. 264(23), 13848-13855.

de Leeuw, R., Mulders, J., Voortman, G. Rombout, F. Damm, J. and Kloosterboer, L. (1996) Structure-function relationship of recombinant follicle stimulating hormone (Puregon). Mol. Hum. Reprod., 2, 361-369.

Lowry O H, Rosebrough N J, Farr A L, Randall R J. (1951) Protein measurement with the Folin phenol reagent. J Biol Chem. 193(1), 265-75.

Lowry, P J, McLean, C, Jones R L and Satgunasingam N. (1976) Purification of anterior pituitary and hypothalamic hormones Clin Pathol Suppl (Assoc Clin Pathol). 7, 16-21.

Pierce J G, and Parsons T F (1981) Glycoprotein hormones: structure and function Annu Rev Biochem. 50 465-495.

Pricer W E Jr, and Ashwell G. (1971). The binding of desialylated glycoproteins by plasma membranes of rat liver. J Biol Chem. 246(15), 4825-33.

Rathnam P, and Saxena B B. (1975). Primary amino acid sequence of follicle-stimulating hormone from human pituitary glands. I. alpha subunit. J Biol Chem.; 250(17): 6735-6746.

Regoeczi E, Debanne M T, Hatton M C, and Koj A. (1978) Elimination of asialofetuin and asialoorosomucoid by the intact rat. Quantitative aspects of the hepatic clearance mechanism. Biochim Biophys Acta. 541(3), 372-84.

Royle L, Radcliffe C M, Dwek R A and Rudd P M (2006) Methods in Molecular Biology, ed I Brockhausen-Schutzbach (Humana Press), 347: Glycobiology protocols, 125-144.

Ryan R J, Keutmann H T, Charlesworth M C, McCormick D J, Milius R P, Calvo F O and Vutyavanich T. (1987). Structure-function relationships of gonadotropins. Recent Prog Horm Res.; 43:383-429.

Saxena B B and Rathnam P. (1976) Amino acid sequence of the beta subunit of follicle-stimulating hormone from human pituitary glands. J Biol Chem. 251(4), 993-1005

Steelman S L, and Pohley F M. (1953) Assay of the follicle stimulating hormone based on the augmentation with human chorionic gonadotropin. Endocrinology. 53(6), 604-616.

Steer C J, and Ashwell G. (1980) Studies on a mammalian hepatic binding protein specific for asialoglycoproteins. Evidence for receptor recycling in isolated rat hepatocytes. J Biol Chem. 255(7), 3008-13.

Svensson E C, Soreghan B, and Paulson J C. (1990) Organization of the beta-galactoside alpha 2,6-sialyltransferase gene. Evidence for the transcriptional regulation of terminal glycosylation. J Biol Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Timossi C M, Barrios de Tomasi J, Zambrano E, Gonzalez R, Ulloa-Aguirre A. (1998). A naturally occurring basically charged human follicle-stimulating hormone (FSH) variant inhibits FSH-induced androgen aromatization and tissue-type plasminogen activator enzyme activity in vitro. Neuroendocrinology. 67(3), 153-163.

Timossi C M, Barrios-de-Tomasi J, Gonzalez-Suarez R, Arranz M C, Padmanabhan V, Conn P M, and Ulloa-Aguirre A. (2000). Differential effects of the charge variants of human follicle-stimulating hormone. J Endocrinol. 165(2), 193-205.

Ulloa-Aguirre, A., Espinoza, R., Damian-Matsumura, P. and Chappel, S. C. (1988) Immunological and biological potencies of the different molecular species of gonadotrophins. Hum. Reprod. 3, 491-501.

Ulloa-Aguirre, A., Cravioto, A., Damián-Matsumura, P. Jimenez, M, Zambrano, E and Diaz-Sanchez, V. (1992) Biological characterization of the naturally occurring analogues of intrapituitary human follicle stimulating hormone. Hum. Reprod. 7, 23-30.

Ulloa-Aguirre A, Midgley A R Jr, Beitins I Z, and Padmanabhan V. (1995). Follicle-stimulating isohormones: characterization and physiological relevance. Endocr Rev. 16(6), 765-787.

Ulloa-Aguirre A, Maldonado A, Damián-Matsumura P, and Timossi C (2001). Endocrine regulation of gonadotropin glycosylation. Arch Med Res. 32(6), 520-532.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

Van Lenten L, and Ashwell G. (1972) The binding of desialylated glycoproteins by plasma membranes of rat liver. Development of a quantitative inhibition assay. J Biol Chem. 247(14), 4633-40.

Wide, L. and Albertsson-Wikland, K. (1990) Change in electrophoretic mobility of human follicle-stimulating hormone in serum after administration of gonadotropin-releasing hormone. J. Clin. Endocrinol. Metab. 70 271-276.

Wide, L. and Bakos, O. (1993). More basic forms of both human follicle-stimulating hormone and luteinizing hormone in serum at midcycle compared with the follicular or luteal phase. J. Clin. Endocrinol. Metab., 76 885-889.

Wide L, Naesson T, Sundström-Poromaa I, Eriksson K. (2007) Sulfonation and sialylation of gonadotropins in women during the menstrual cycle, after menopause, and with polycystic ovarian syndrome and in men. J Clin Endocrinol Metab.; 92(11), 4410-4417.

Zambrano E, Zarñán T, Olivares A, Barrios-de-Tomasi J, and Ulloa-Aguirre A. (1999). Receptor binding activity and in vitro biological activity of the human FSH charge isoforms as disclosed by heterologous and homologous assay systems: implications for the structure-function relationship of the FSH variants. Endocrine. 10(2), 113-121.

Zhang X, Lok S H, and Kon O L (1998) Stable expression of human alpha-2,6-sialyltransferase in Chinese hamster ovary cells: functional consequences for human erythropoietin expression and bioactivity. Biochim Biophys Acta. 1425(3), 441-452.

---

Sequences

Follicle stimulating hormone alpha polypeptide
Accession number AH007338
Nucleotide sequence of FSH alpha (SEQ ID NO: 1)

```
  1 ATGGATTACT ACAGAAAATA TGCAGCTATC TTTCTGGTCA CATTGTCGGT GTTTCTGCAT
 61 GTTCTCCATT CCGCTCCTGA TGTGCAGGAT TGCCCAGAAT GCACGCTACA GGAAAACCCA
121 TTCTTCTCCC AGCCGGGTGC CCCAATACTT CAGTGCATGG GCTGCTGCTT CTCTAGAGCA
181 TATCCCACTC CACTAAGGTC CAAGAAGACG ATGTTGGTCC AAAAGAACGT CACCTCAGAG
241 TCCACTTGCT GTGTAGCTAA ATCATATAAC AGGGTCACAG TAATGGGGGG TTTCAAAGTG
301 GAGAACCACA CGGCGTGCCA CTGCAGTACT TGTTATTATC ACAAATCTTA A
```

Protein sequence of FSH alpha (SEQ ID NO: 5)

```
  1 MKTLQFFFLF CCWKAICCNS CELTNITIAI EKEECRFCIS INTTWCAGYC YTRDLVYKDP
 61 ARPKIQKTCT FKELVYETVR VPGCAHHADS LYTYPVATQC HCGKCDSDST DCTVRGLGPS
121 YCSFGEMKE
```

Sequences

Follicle stimulating hormone beta polypeptide
Accession number NM_000510
Nucleotide sequence of FSH beta (SEQ ID NO: 2)

```
  1 ATGAAGACAC TCCAGTTTTT CTTCCTTTTC TGTTGCTGGA AAGCAATCTG CTGCAATAGC
 61 TGTGAGCTGA CCAACATCAC CATTGCAATA GAGAAAGAAG AATGTCGTTT CTGCATAAGC
121 ATCAACACCA CTTGGTGTGC TGGCTACTGC TACACCAGGG ATCTGGTGTA TAAGGACCCA
181 GCCAGGCCCA AAATCCAGAA AACATGTACC TTCAAGGAAC TGGTATATGA AACAGTGAGA
241 GTGCCCGGCT GTGCTCACCA TGCAGATTCC TTGTATACAT ACCCAGTGGC CACCCAGTGT
301 CACTGTGGCA AGTGTGACAG CGACAGCACT GATTGTACTG TGCGAGGCCT GGGGCCCAGC
361 TACTGCTCCT TTGGTGAAAT GAAAGAATAA
```

Protein sequence of FSH beta (SEQ ID NO: 6)

```
  1 MKTLQFFFLF CCWKAICCNS CELTNITIAI EKEECRFCIS INTTWCAGYC YTRDLVYKDP
 61 ARPKIQKTCT FKELVYETVR VPGCAHHADS LYTYPVATQC HCGKCDSDST DCTVRGLGPS
121 YCSFGEMKE
```

Beta-galactoside alpha-2,3-sialyltransferase 4
Accession Number L23767
Nucleotide sequence of ST3GAL4

(SEQ ID NO: 3)

```
  1 ATGTGTCCTG CAGGCTGGAA GCTCCTGGCC ATGTTGGCTC TGGTCCTGGT CGTCATGGTG
 61 TGGTATTCCA TCTCCCGGGA AGACAGGTAC ATCGAGCTTT TTTATTTTCC CATCCCAGAG
121 AAGAAGGAGC CGTGCCTCCA GGGTGAGGCA GAGAGCAAGG CCTCTAAGCT CTTTGGCAAC
181 TACTCCCGGG ATCAGCCCAT CTTCCTGCGG CTTGAGGATT ATTTCTGGGT CAAGACGCCA
241 TCTGCTTACG AGCTGCCCTA TGGGACCAAG GGGAGTGAGG ATCTGCTCCT CCGGGTGCTA
301 GCCATCACCA GCTCCTCCAT CCCCAAGAAC ATCCAGAGCC TCAGGTGCCG CCGCTGTGTG
361 GTCGTGGGGA ACGGGCACCG GCTGCGGAAC AGCTCACTGG GAGATGCCAT CAACAAGTAC
421 GATGTGGTCA TCAGATTGAA CAATGCCCCA GTGGCTGGCT ATGAGGGTGA CGTGGGCTCC
481 AAGACCACCA TGCGTCTCTT CTACCCTGAA TCTGCCCACT TCGACCCCAA AGTAGAAAAC
541 AACCCAGACA CACTCCTCGT CCTGGTAGCT TTCAAGGCAA TGGACTTCCA CTGGATTGAG
601 ACCATCCTGA GTGATAAGAA GCGGGTGCGA AAGGGTTTCT GGAAACAGCC TCCCCTCATC
661 TGGGATGTCA ATCCTAAACA GATTCGGATT CTCAACCCCT TCTTCATGGA GATTGCAGCT
721 GACAAACTGC TGAGCCTGCC AATGCAACAG CCACGGAAGA TTAAGCAGAA GCCCACCACG
781 GGCCTGTTGG CCATCACGCT GGCCCTCCAC CTCTGTGACT TGGTGCACAT TGCCGGCTTT
841 GGCTACCCAG ACGCCTACAA CAAGAAGCAG ACCATTCACT ACTATGAGCA GATCACGCTC
901 AAGTCCATGG CGGGGTCAGG CCATAATGTC TCCCAAGAGG CCCTGGCCAT TAAGCGGATG
961 CTGGAGATGG GAGCTATCAA GAACCTCACG TCCTTCTGA
```

Protein Sequence of ST3GAL4

(SEQ ID NO: 7)

```
  1 MCPAGWKLLA MLALVLVVMV WYSISREDRY IELFYFPIPE KKEPCLQGEA ESKASKLFGN
 61 YSRDQPIFLR LEDYFWVKTP SAYELPYGTK GSEDLLLRVL AITSSSIPKN IQSLRCRRCV
121 VVGNGHRLRN SSLGDAINKY DVVIRLNNAP VAGYEGDVGS KTTMRLFYPE SAHFDPKVEN
181 NPDTLLVLVA FKAMDFHWIE TILSDKKRVR KGFWKQPPLI WDVNPKQIRI LNPFFMEIAA
241 DKLLSLPMQQ PRKIKQKPTT GLLAITLALH LCDLVHIAGF GYPDAYNKKQ TIHYYEQITL
301 KSMAGSGHNV SQEALAIKRM LEMGAIKNLT SF
```

Beta-galactosamide alpha-2,6-sialyltransferase 1
Accession number NM_003032
Nucleotide sequence of ST6GAL1

(SEQ ID NO: 4)

```
   1 ATGATTCACA CCAACCTGAA GAAAAAGTTC AGCTGCTGCG TCCTGGTCTT TCTTCTGTTT
  61 GCAGTCATCT GTGTGTGGAA GGAAAAGAAG AAAGGGAGTT ACTATGATTC CTTTAAATTG
 121 CAAACCAAGG AATTCCAGGT GTTAAAGAGT CTGGGGAAAT TGGCCATGGG GTCTGATTCC
 181 CAGTCTGTAT CCTCAAGCAG CACCCAGGAC CCCCACAGGG GCCGCCAGAC CCTCGGCAGT
 241 CTCAGAGGCC TAGCCAAGGC CAAACCGAGG GCCTCCTTCC AGGTGTGGAA CAAGGACAGC
 301 TCTTCCAAAA ACCTTATCCC TAGGCTGCAA AAGATCTGGA AGAATTACCT AAGCATGAAC
 361 AAGTACAAAG TGTCCTACAA GGGGCCAGGA CCAGGCATCA AGTTCAGTGC AGAGGCCCTG
 421 CGCTGCCACC TCCGGGACCA TGTGAATGTA TCCATGGTAG AGGTCACAGA TTTTCCCTTC
 481 AATACCTCTG AATGGGAGGG TTATCTGCCC AAGGAGAGCA TTAGGACCAA GGCTGGGCCT
 541 TGGGGCAGGT GTGCTGTTGT GTCGTCAGCG GGATCTCTGA AGTCCTCCCA ACTAGGCAGA
 601 GAAATCGATG ATCATGACGC AGTCCTGAGG TTTAATGGGG CACCCACAGC CAACTTCCAA
 661 CAAGATGTGG GCACAAAAAC TACCATTCGC CTGATGAACT CTCAGTTGGT TACCACAGAG
 721 AAGCGCTTCC TCAAAGACAG TTTGTACAAT GAAGGAATCC TAATTGTATG GGACCCATCT
 781 GTATACCACT CAGATATCCC AAAGTGGTAC CAGAATCCGG ATTATAATTT CTTTAACAAC
 841 TACAAGACTT ATCGTAAGCT GCACCCCAAT CAGCCCTTTT ACATCCTCAA GCCCCAGATG
 901 CCTTGGGAGC TATGGGACAT TCTTCAAGAA ATCTCCCCAG AAGAGATTCA GCCAAACCCC
 961 CCATCCTCTG GGATGCTTGG TATCATCATC ATGATGACGC TGTGTGACCA GGTGGATATT
1021 TATGAGTTCC TCCCATCCAA GCGCAAGACT GACGTGTGCT ACTACTACCA GAAGTTCTTC
1081 GATAGTGCCT GCACGATGGG TGCCTACCAC CCGCTGCTCT ATGAGAAGAA TTTGGTGAAG
1141 CATCTCAACC AGGGCACAGA TGAGGACATC TACCTGCTTG GAAAGCCAC ACTGCCTGGC
1201 TTCCGGACCA TTCACTGCTA A
```

Sequences

Protein Sequence of ST6GAL1

(SEQ ID NO: 8)

```
  1 MIHTNLKKKF SCCVLVFLLF AVICVWKEKK KGSYYDSFKL QTKEFQVLKS LGKLAMGSDS
 61 QSVSSSSTQD PHRGRQTLGS LRGLAKAKPE ASFQVWNKDS SSKNLIPRLQ KIWKNYLSMN
121 KYKVSYKGPG PGIKFSAEAL RCHLRDHVNV SMVEVTDFPF NTSEWEGYLP KESIRTKAGP
181 WGRCAVVSSA GSLKSSQLGR EIDDHDAVLR FNGAPTANFQ QDVGTKTTIR LMNSQLVTTE
241 KRFLKDSLYN EGILIVWDPS VYHSDIPKWY QNPDYNFFNN YKTYRKLHPN QPFYILKPQM
301 PWELWDILQE ISPEEIQPNP PSSGMLGIII MMTLCDQVDI YEFLPSKRKT DVCYYYQKFF
361 DSACTMGAYH PLLYEKNLVK HLNQGTDEDI YLLGKATLPG FRTIHC
```

The invention claimed is:

1. Recombinant follicle stimulating hormone (FSH) comprising α2,3- and α2,6-sialylation, produced or expressed in a human cell line, wherein from 5% to 20% of the total sialylation of the recombinant FSH is α2,6-sialylation.

2. The recombinant FSH according to claim 1, wherein the human cell line has been modified using an α2,3-sialyltransferase.

3. The recombinant FSH according to claim 1, wherein the human cell line has endogenous α2,6-sialyltransferase activity.

4. The recombinant FSH according to claim 1, wherein the human cell line is a PER.C6® cell line (European Collection of Cell Cultures deposit number 96022940).

5. The recombinant FSH according to claim 1, wherein the human cell line is a PER.C6® cell line (European Collection of Cell Cultures deposit number 96022940) that has endogenous α2,6-sialyltransferase activity.

* * * * *

SEQUENCE LISTING

<160> NUMBER OF SEQ ID NOS: 16

<210> SEQ ID NO 1
<211> LENGTH: 351
<212> TYPE: DNA
<213> ORGANISM: Artificial Sequence
<220> FEATURE:
<223> OTHER INFORMATION: SEQ ID 1 Nucleotide Sequence of FSH alpha

<400> SEQUENCE: 1

```
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
tatcccactc cactaaggtc caagaagacg atgttggtcc aaaagaacgt cacctcagag     240
tccacttgct gtgtagctaa atcatataac agggtcacag taatggggg tttcaaagtg     300
gagaaccaca cggcgtgcca ctgcagtact tgttattatc acaaatctta a             351
```

<210> SEQ ID NO 2
<211> LENGTH: 390
<212> TYPE: DNA
<213> ORGANISM: Artificial Sequence
<220> FEATURE:
<223> OTHER INFORMATION: SEQ ID 2 Nucleotide Sequence of FSH beta

<400> SEQUENCE: 2

```
atgaagacac tccagttttt cttccttttc tgttgctgga agcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taggaccca     180
gccaggccca aaatccagaa acatgtacc ttcaaggaac tggtatatga acagtgaga     240
gtgcccggct gtgctcacca tgcagattcc ttgtatacat acccagtggc cacccagtgt     300
cactgtggca gtgtgacag cgacagcact gattgtactg tgcgaggcct ggggcccagc     360
tactgctcct tggtgaaat gaaagaataa                                       390
```

<210> SEQ ID NO 3
<211> LENGTH: 999
<212> TYPE: DNA
<213> ORGANISM: Artificial Sequence
<220> FEATURE:
<223> OTHER INFORMATION: SEQ ID 3 Nucleotide Sequence of ST3GAL4

<400> SEQUENCE: 3

```
atgtgtcctg caggctggaa gctcctggcc atgttggctc tggtcctggt cgtcatggtg      60
tggtattcca tctcccggga agacaggtac atcgagcttt tttatttcc catcccagag     120
```

| | | |
|---|---|---|
| aagaaggagc cgtgcctcca gggtgaggca gagagcaagg cctctaagct ctttggcaac | 180 |
| tactcccggg atcagcccat cttcctgcgg cttgaggatt atttctgggt caagacgcca | 240 |
| tctgcttacg agctgcccta tgggaccaag gggagtgagg atctgctcct ccgggtgcta | 300 |
| gccatcacca gctcctccat ccccaagaac atccagagcc tcaggtgccg ccgctgtgtg | 360 |
| gtcgtgggga acgggcaccg gctgcggaac agctcactgg gagatgccat caacaagtac | 420 |
| gatgtggtca tcagattgaa caatgcccca gtggctggct atgagggtga cgtgggctcc | 480 |
| aagaccacca tgcgtctctt ctaccctgaa tctgcccact tcgacccaa agtagaaaac | 540 |
| aacccagaca cactcctcgt cctggtagct ttcaaggcaa tggacttcca ctggattgag | 600 |
| accatcctga gtgataagaa gcgggtgcga aagggtttct ggaaacagcc tcccctcatc | 660 |
| tgggatgtca atcctaaaca gattcggatt ctcaacccct tcttcatgga gattgcagct | 720 |
| gacaaactgc tgagcctgcc aatgcaacag ccacggaaga ttaagcagaa gcccaccacg | 780 |
| ggcctgttgg ccatcacgct ggccctccac ctctgtgact tggtgcacat tgccggcttt | 840 |
| ggctacccag acgcctacaa caagaagcag accattcact actatgagca gatcacgctc | 900 |
| aagtccatgg cggggtcagg ccataatgtc tcccaagagg ccctggccat taagcggatg | 960 |
| ctggagatgg gagctatcaa gaacctcacg tccttctga | 999 |

<210> SEQ ID NO 4
<211> LENGTH: 1221
<212> TYPE: DNA
<213> ORGANISM: Artificial Sequence
<220> FEATURE:
<223> OTHER INFORMATION: SEQ ID 4 Nucleotide Sequence of ST6GAL1

<400> SEQUENCE: 4

| | | |
|---|---|---|
| atgattcaca ccaacctgaa gaaaagttc agctgctgcg tcctggtctt cttctgtttt | 60 |
| gcagtcatct gtgtgtggaa ggaaaagaag aagggagtt actatgattc ctttaaattg | 120 |
| caaaccaagg aattccaggt gttaaagagt ctggggaaat tggccatggg gtctgattcc | 180 |
| cagtctgtat cctcaagcag cacccaggac ccccacaggg gccgccagac cctcggcagt | 240 |
| ctcagaggcc tagccaaggc caaaccagag gcctccttcc aggtgtggaa caaggacagc | 300 |
| tcttccaaaa accttatccc taggctgcaa aagatctgga agaattacct aagcatgaac | 360 |
| aagtacaaag tgtcctacaa ggggccagga ccaggcatca agttcagtgc agaggccctg | 420 |
| cgctgccacc tccgggacca tgtgaatgta tccatggtag aggtcacaga ttttcccttc | 480 |
| aatacctctg aatgggaggg ttatctgccc aaggagagca ttaggaccaa ggctgggcct | 540 |
| tggggcaggt gtgctgttgt gtcgtcagcg ggatctctga agtcctccca actaggcaga | 600 |
| gaaatcgatg atcatgacgc agtcctgagg tttaatgggg cacccacagc caacttccaa | 660 |
| caagatgtgg gcacaaaaac taccattcgc ctgatgaact ctcagttggt taccacagag | 720 |
| aagcgcttcc tcaaagacag tttgtacaat gaaggaatcc taattgtatg gaccccatct | 780 |
| gtataccact cagatatccc aaagtggtac cagaatccgg attataattt cttttaacaac | 840 |
| tacaagactt atcgtaagct gcaccccaat cagcccttt acatcctcaa gccccagatg | 900 |
| ccttgggagc tatgggacat tcttcaagaa atctccccag aagagattca gccaaacccc | 960 |
| ccatcctctg ggatgcttgg tatcatcatc atgatgacgc tgtgtgacca ggtggatatt | 1020 |
| tatgagttcc tcccatccaa gcgcaagact gacgtgtgct actactacca gaagttcttc | 1080 |
| gatagtgcct gcacgatggg tgcctaccac ccgctgctct atgagaagaa tttggtgaag | 1140 |

```
catctcaacc agggcacaga tgaggacatc tacctgcttg gaaaagccac actgcctggc    1200
ttccggacca ttcactgcta a                                              1221
```

<210> SEQ ID NO 5
<211> LENGTH: 129
<212> TYPE: PRT
<213> ORGANISM: Artificial Sequence
<220> FEATURE:
<223> OTHER INFORMATION: Protein Sequence of FSH alpha

<400> SEQUENCE: 5

```
Met Lys Thr Leu Gln Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
            115                 120                 125

Glu
```

<210> SEQ ID NO 6
<211> LENGTH: 129
<212> TYPE: PRT
<213> ORGANISM: Artificial Sequence
<220> FEATURE:
<223> OTHER INFORMATION: Protein Sequence of FSH beta

<400> SEQUENCE: 6

```
Met Lys Thr Leu Gln Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
            115                 120                 125

Glu
```

<210> SEQ ID NO 7
<211> LENGTH: 332
<212> TYPE: PRT
<213> ORGANISM: Artificial Sequence
<220> FEATURE:
<223> OTHER INFORMATION: Protein Sequence of ST3GAL4

<400> SEQUENCE: 7

```
Met Cys Pro Ala Gly Trp Lys Leu Leu Ala Met Leu Ala Leu Val Leu
1               5                   10                  15

Val Val Met Val Trp Tyr Ser Ile Ser Arg Glu Asp Arg Tyr Ile Glu
            20                  25                  30

Leu Phe Tyr Phe Pro Ile Pro Glu Lys Lys Glu Pro Cys Leu Gln Gly
        35                  40                  45

Glu Ala Glu Ser Lys Ala Ser Lys Leu Phe Gly Asn Tyr Ser Arg Asp
    50                  55                  60

Gln Pro Ile Phe Leu Arg Leu Glu Asp Tyr Phe Trp Val Lys Thr Pro
65                  70                  75                  80

Ser Ala Tyr Glu Leu Pro Tyr Gly Thr Lys Gly Ser Glu Asp Leu Leu
                85                  90                  95

Leu Arg Val Leu Ala Ile Thr Ser Ser Ser Ile Pro Lys Asn Ile Gln
            100                 105                 110

Ser Leu Arg Cys Arg Arg Cys Val Val Val Gly Asn Gly His Arg Leu
        115                 120                 125

Arg Asn Ser Ser Leu Gly Asp Ala Ile Asn Lys Tyr Asp Val Val Ile
    130                 135                 140

Arg Leu Asn Asn Ala Pro Val Ala Gly Tyr Glu Gly Asp Val Gly Ser
145                 150                 155                 160

Lys Thr Thr Met Arg Leu Phe Tyr Pro Glu Ser Ala His Phe Asp Pro
                165                 170                 175

Lys Val Glu Asn Asn Pro Asp Thr Leu Leu Val Leu Val Ala Phe Lys
            180                 185                 190

Ala Met Asp Phe His Trp Ile Glu Thr Ile Leu Ser Asp Lys Lys Arg
        195                 200                 205

Val Arg Lys Gly Phe Trp Lys Gln Pro Pro Leu Ile Trp Asp Val Asn
    210                 215                 220

Pro Lys Gln Ile Arg Ile Leu Asn Pro Phe Phe Met Glu Ile Ala Ala
225                 230                 235                 240

Asp Lys Leu Leu Ser Leu Pro Met Gln Gln Pro Arg Lys Ile Lys Gln
                245                 250                 255

Lys Pro Thr Thr Gly Leu Leu Ala Ile Thr Leu Ala Leu His Leu Cys
            260                 265                 270

Asp Leu Val His Ile Ala Gly Phe Gly Tyr Pro Asp Ala Tyr Asn Lys
        275                 280                 285

Lys Gln Thr Ile His Tyr Tyr Glu Gln Ile Thr Leu Lys Ser Met Ala
    290                 295                 300

Gly Ser Gly His Asn Val Ser Gln Glu Ala Leu Ala Ile Lys Arg Met
305                 310                 315                 320

Leu Glu Met Gly Ala Ile Lys Asn Leu Thr Ser Phe
                325                 330
```

<210> SEQ ID NO 8
<211> LENGTH: 406
<212> TYPE: PRT
<213> ORGANISM: Artificial Sequence
<220> FEATURE:
<223> OTHER INFORMATION: Protein Sequence of ST6GAL1

<400> SEQUENCE: 8

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
                20                  25                  30

Ser Tyr Tyr Asp Ser Phe Lys Leu Gln Thr Lys Glu Phe Gln Val Leu
                35                  40                  45

Lys Ser Leu Gly Lys Leu Ala Met Gly Ser Asp Ser Gln Ser Val Ser
        50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
                115                 120                 125

Pro Gly Pro Gly Ile Lys Phe Ser Ala Glu Ala Leu Arg Cys His Leu
        130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
                180                 185                 190

Leu Lys Ser Ser Gln Leu Gly Arg Glu Ile Asp Asp His Asp Ala Val
        195                 200                 205

Leu Arg Phe Asn Gly Ala Pro Thr Ala Asn Phe Gln Gln Asp Val Gly
210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
                260                 265                 270

Pro Asp Tyr Asn Phe Phe Asn Asn Tyr Lys Thr Tyr Arg Lys Leu His
                275                 280                 285

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
                340                 345                 350

Cys Tyr Tyr Tyr Gln Lys Phe Phe Asp Ser Ala Cys Thr Met Gly Ala
                355                 360                 365

Tyr His Pro Leu Leu Tyr Glu Lys Asn Leu Val Lys His Leu Asn Gln
        370                 375                 380

Gly Thr Asp Glu Asp Ile Tyr Leu Leu Gly Lys Ala Thr Leu Pro Gly
385                 390                 395                 400

Phe Arg Thr Ile His Cys
                405
```

<210> SEQ ID NO 9
<211> LENGTH: 39
<212> TYPE: DNA
<213> ORGANISM: Artificial Sequence
<220> FEATURE:
<223> OTHER INFORMATION: PCR Primer FSHa-fw

<400> SEQUENCE: 9
ccaggatccg ccaccatgga ttactacaga aaaatatgc                          39

<210> SEQ ID NO 10
<211> LENGTH: 31
<212> TYPE: DNA
<213> ORGANISM: Artificial Sequence
<220> FEATURE:
<223> OTHER INFORMATION: PCR Primer FSHa-rev

<400> SEQUENCE: 10
ggatggctag cttaagattt gtgataataa c                                  31

<210> SEQ ID NO 11
<211> LENGTH: 35
<212> TYPE: DNA
<213> ORGANISM: Artificial Sequence
<220> FEATURE:
<223> OTHER INFORMATION: PCR Primer FSHb-fw

<400> SEQUENCE: 11
ccaggcgcgc caccatgaag acactccagt ttttc                              35

<210> SEQ ID NO 12
<211> LENGTH: 36
<212> TYPE: DNA
<213> ORGANISM: Artificial Sequence
<220> FEATURE:
<223> OTHER INFORMATION: PCR Primer FSHb-rev

<400> SEQUENCE: 12
ccgggttaac ttattattct ttcatttcac caaagg                             36

<210> SEQ ID NO 13
<211> LENGTH: 37
<212> TYPE: DNA
<213> ORGANISM: Artificial Sequence
<220> FEATURE:
<223> OTHER INFORMATION: PCR Primer 2,3STfw

<400> SEQUENCE: 13
ccaggatccg ccaccatgtg tcctgcaggc tggaagc                            37

<210> SEQ ID NO 14
<211> LENGTH: 35
<212> TYPE: DNA
<213> ORGANISM: Artificial Sequence
<220> FEATURE:
<223> OTHER INFORMATION: PCR Primer 2,3STrev

<400> SEQUENCE: 14 ttttttttctt aagtcagaag gacgtgaggt tcttg                             35

<210> SEQ ID NO 15
<211> LENGTH: 36
<212> TYPE: DNA
<213> ORGANISM: Artificial Sequence
<220> FEATURE:
<223> OTHER INFORMATION: PCR Primer 2,6STfw -continued

```
<400> SEQUENCE: 15
ccaggatccg ccaccatgat tcacaccaac ctgaag                                36

<210> SEQ ID NO 16
<211> LENGTH: 32
<212> TYPE: DNA
<213> ORGANISM: Artificial Sequence
<220> FEATURE:
<223> OTHER INFORMATION: PCR Primer 2,6STrev

<400> SEQUENCE: 16 ttttttctt aagttagcag tgaatggtcc gg                                      32
```